(12) United States Patent
Schalk

(10) Patent No.: US 7,790,413 B2
(45) Date of Patent: Sep. 7, 2010

(54) SESQUITERPENE SYNTHASES AND METHODS OF THEIR USE

(75) Inventor: Michel Schalk, Collonges-Sous-Saleve (FR)

(73) Assignee: Firmenich SA, Geneva (CH)

( * ) Notice: Subject to any disclaimer, the term of this patent is extended or adjusted under 35 U.S.C. 154(b) by 89 days.

(21) Appl. No.: 11/914,536

(22) PCT Filed: Jun. 8, 2006

(86) PCT No.: PCT/IB2006/051831

§ 371 (c)(1),
(2), (4) Date: Nov. 15, 2007

(87) PCT Pub. No.: WO2006/134523

PCT Pub. Date: Dec. 21, 2006

(65) Prior Publication Data

US 2008/0268500 A1  Oct. 30, 2008

(30) Foreign Application Priority Data

Jun. 17, 2005  (EP)  ................................. 05105381

(51) Int. Cl.
| | |
|---|---|
| C12P 21/06 | (2006.01) |
| C12P 7/64 | (2006.01) |
| C12N 9/00 | (2006.01) |
| C12N 9/88 | (2006.01) |
| C12N 1/20 | (2006.01) |
| C07H 21/04 | (2006.01) |
| C12N 15/82 | (2006.01) |

(52) U.S. Cl. .................. 435/69.1; 435/91.1; 435/134; 435/183; 435/232; 435/252.3; 435/254.11; 435/320.1; 435/419; 536/23.1; 536/23.2; 800/278; 800/281; 800/298

(58) Field of Classification Search ................... None
See application file for complete search history.

(56) References Cited

U.S. PATENT DOCUMENTS

2007/0039067 A1* 2/2007 Feldmann et al. ........... 800/278

FOREIGN PATENT DOCUMENTS

WO  WO 02/064764  8/2002
WO  WO 2004/031376  4/2004

OTHER PUBLICATIONS

Broun et al., Catalytic plasticity of fatty acid modification enzymes underlying chemical diversity of plant lipids. Science, 1998, vol. 282: 1315-1317.*
Guo et al., Protein tolerance to random amino acid change. PNAS., 2004, vol. 101 (25): 9205-9210.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol.,2001, vol. 183 (8): 2405-2410.*
Wishart et al., A single mutation converts a novel phosphotyrosine binding domain into a dual-specificity phosphatase. J. Biol. Chem., 1995, vol. 270(45): 26782-26785.*
Witkowski et a l., Conversion of b-ketoacyl synthase to a Malonyl Decarboxylase by replacement of the active cysteine with glutamine. Biochemistry, 1999, vol. 38: 11643-11650.*
Cameron ER., Recent advances in transgenic technology. 1997, vol. 7: 253-265.*
Devos et al., Practical limits of function prediction. Proteins: Structure, Function, and Genetics. 2000, vol. 41: 98-107.*
Kappel et al., Regulating gene expression in transgenic animals. Current Opinion in Biotechnology 1992, vol. 3: 548-553.*
Mullins et al., Transgenesis in the rat and larger mammals. J. Clin. Invest., 1996, vol. 97 (7): 1557-1560.*
Mullins et al., Transgenesis in the rat and larger mammals. J. Clin. Invest., 1996, vol. 97 (7): 1557-1560.*
Whisstock et al., Prediction of protein function from protein sequence. Q. Rev. Biophysics., 2003, vol. 36 (3): 307-340.*
Wigley et al., Site-specific transgene insertion: an approach. Reprod. Fert. Dev., 1994, vol. 6: 585-588.*
International Search Report for PCT/IB2006/051831, Jun. 17, 2005.
Database Sequence Abstract: XP002417462, "Zea Mays B73 Terpene Synthase 4 (TPS4) mRNA, Complete cds." (2004).
Database Sequence Abstract: XP002417463, "Zea Mays B73 Terpene Synthase 5 (TPS5) mRNA, complete cds.", (2004).
Database Sequence Abstract: XP002417464, "Zea Mays Delprim Terpene Synthase 4 (TPS4) mRNA, Complete cds.", (2004).
Database Sequence Abstract: XP002417465, "Zea Mays Delprim Terpene Synthase 5 (TPS5) mRNA,TPS5-1 Allele, Complete cds.", (2004).
Database Sequence Abstract: XP002417466, Sasaki et al, "Putative Sesquiterpene Cyclase 1", (2005).
G. Kollner Tobias et al., XP002344231, "The Variability Of Sesquiterpenes Emitted From Two Zea Mays Cultivars Is Controlled By Allelic Variation Of Two Terpene Synthase Genes Encoding Stereoselective Multiple Product Enzymes", The Plant Cell, vol. 16, No. 5, pp. 1115-1131, (2004).
N. H. Andersen, XP002344233, "Biogenetic Implications Of The Antipodal Sesquiterpenes Of Vetiver Oil", Phytochemistry, vol. 9, No. 1, pp. 145-151, (1970).
P. M. Dewick, XP002344232, "The Biosynthesis Of C5-C25 Terpenoid Compounds", Natural Product Reports, vol. 19, No. 2, pp. 181-222, (2004).

* cited by examiner

*Primary Examiner*—Ganapathirama Raghu
(74) *Attorney, Agent, or Firm*—Winston & Strawn LLP

(57) ABSTRACT

The present invention relates to terpene synthases that are capable of synthesizing mono-, bi- and/or tri-cyclic sesquiterpenes having a $C_2$-$C_7$ or a $C_3$-$C_7$ bond, starting from an acyclic pyrophosphate terpene precursor, farnesyl- pyrophosphate. Accordingly, for the first time, sesquiterpene synthases catalyzing the cyclization to the santalene and bergamotene carbon skeleton are disclosed. The present invention further relates to nucleic acid sequences encoding the sesquiterpene synthases and to methods for making terpenoids.

17 Claims, 7 Drawing Sheets

Figure 2

```
              10        20        30        40        50        60        70
     ....|....|....|....|....|....|....|....|....|....|....|....|....|....|.
     ---------------------------------------IVGVYYEPRY-SRGRIILKKVLGIVSIL 27  CA711
     --------------------------------------MLGVVYEPYYPAYSRIYMTKFIVLASLL 28  CA717
     --------------------------------------PIWCIMNKSTYRRARLILAKIIVLTSLL 28  CA782
     --------------------------------------AAGGCIEPKY-SSFRIGFAKFCSLATVM 27  CA783
     --------------------------------------MNGYCYHPPY-SHSRIQTKITSFVTII  27  CA733
     NLVQALHRRELAEVTRWWKESRLGEGDVDYSFARDRVVECFFCAACIAPEPRL-ADCREVLAKTGALIVHL 70  CA725
     ----------TNSIFRWW---RTLYKDVKLSYCRDRLVEMYFWTIEMLPWEEC-SRSRIVLTKVIAFAILM 57  CA731
```

CA711 = SEQ ID NO : 8

CA717 = SEQ ID NO : 9

CA782 = SEQ ID NO : 10

CA783 = SEQ ID NO : 11

CA733 = SEQ ID NO : 12

CA725 = SEQ ID NO : 13

CA731 = SEQ ID NO : 14

Figure 3

```
              10         20         30         40         50         60         70
              ....|....|....|....|....|....|....|....|....|....|....|....|....|....|
Vet717        ------MASSSPVPLVTQVQ----RRPQ------------------------------TETPSPWG  26
Vet733        ----MALPVAHRYSSEAEEL----REAT------------------------------TEHPSLWG  28
Vet775        MWNCSLTISATAASEPLRQWPGGISWRRESRLQCSAATTRHDDDLVLDNKGDNRLRENTGADIEQPSIWG  70

80         90        100        110        120        130        140
              ....|....|....|....|....|....|....|....|....|....|....|....|....|....|
Vet717        DFFIHHVP----CTPSQFLSMERAQRKKEEVRQIILENFASSNIVRKILVDTLQRIGVDYYKEEIDN   92
Vet733        DFFITYQP----PTAAQQAYMEERAEVLREDVRKILRD---STQLPETINLILTLQRLGLDYYENEIDK   91
Vet775        DIFLGNSNPAAAASSQQQIQMEERADKLREEVAKNIAS---STTTASRLQLIDALERICLDELREEIGA  137

150        160        170        180        190        200        210
              ....|....|....|....|....|....|....|....|....|....|....|....|....|....|
Vet717        LLHSIFDDKDGGSDNLYITSLRFYLLRKHGYGVSSDVFENFRDEQGNISSDDISCLLMLYLAAHLRTHGE  162
Vet733        LLHRIYN-SDYIDKDINLVSLRFYLLRKNGYDVSSDVFLSFKTDEGGFAYGDTISLLILYNAAYLRRHGE  160
Vet775        ALAQIET-ADVSDYDIETVALWFCLLRKHRYMVSPDVEYRFKDEDGGFLVNSPKDLLLLYNAAHMRTHGE  206

220        230        240        250        260        270        280
              ....|....|....|....|....|....|....|....|....|....|....|....|....|....|
Vet717        EILDNIITENKSHLQSILLENLEPELREEVQCTLETPRFRRVKRVEARRYISVYEKNTTRDATILEFAKL  232
Vet733        KVLDEAISFTRRLQDILELPASP-FAKEVSASLHTPLFRRVGILEARNYIPIYEKDATVKEAILELAKL  229
Vet775        IILEEAVLFSQRHLETMVPYMEGS-LAREIKSALDIPIPRRPHIYEYKYYISMYEKDGMVDEKVLQLAKL  275

290        300        310        320        330        340        350
              ....|....|....|....|....|....|....|....|....|....|....|....|....|....|
Vet717        DVNILQAIYCDELKELTWWKDFQSQTDLSFARDRMVELHFWMLGVVYEPYYPYSRLMTKFIVLASLLD   302
Vet733        NENLQQIVFCEELKHCTWWKEFLAKSKMTFVRDRIVEYYFWMNGACYHPPYSSRIIQTKITSFVTLLD   299
Vet775        NSNIMQLHHQHELGIVSRWWNDINIESKIPHVRDRLVECYLWILGVYYEPCYSRARIILTMTTAMVTLLD  345

360        370        380        390        400        410        420
              ....|....|....|....|....|....|....|....|....|....|....|....|....|....|
Vet717        DLYDSYSTTEESNAEIAAMQRWDDRTTEHLPACLRALFINIVKTTNEIEEEIKLMKNKHADLIKRLVIDT  372
Vet733        DMEDIYGTTEECMKFVEAIGRWDESAVPLLPEYMKGFYLFLLDTFHSFEEELGPQKYRVILYLKHAMERL  369
Vet775        DTYDSYATPEECELFTKCIESWDSMGAQDLPERMKYGLEKIFDSCEIIERMLHQEEKYRIWYLRQSIKDL  415

430        440        450        460        470        480        490
              ....|....|....|....|....|....|....|....|....|....|....|....|....|....|
Vet717        ARFYHAEVEWRDQHYIPTDIEEHLQISTRSSVCMQITNLALISIGEVITRKDVDWALIFPKIIRAACIVG  442
Vet733        VQQYYNETKWRDEDYVPKTMSEHLQVSMESIACLPITCAAFVGMGDIITKETLEWLLSFPQFLMSFGIYV  439
Vet775        VISYSVEVKMLQEGYIPKSVEEHLKISLITVGYPILACYSFVGMHDIATKDCLDWVSSIPKNVEALSVIL  485

500        510        520        530        540        550        560
              ....|....|....|....|....|....|....|....|....|....|....|....|....|....|
Vet717        RVGNDIVSHEREQTSEHVGSTVQTCMKQYGVTREFANEKLRVIIEEWMDIVEECIEQ---KRPMALLET  509
Vet733        RLSNDVASTMREQTKDHSASTVHCYMKEHGTTMNLACEKIKELAEDKWKDMLEQCIALT--ELPKVIPRT  507
Vet775        RLVDLESYEREQLVPHVASTTDSYMKEHNVSIEVAREQIYILKEESWKDFNNEWLNPDNNVYPKQLLER  555

570        580        590        600
              ....|....|....|....|....|....|....|..
Vet717        AVNVARTMDFMYK-REDAYTLSFSLKDVIASMYVNSVRAC--  548    SEQ ID NO : 4
Vet733        VELFARTIVNMYKNDHDGFTSSEALKEAIELLVKPVPN---  546    SEQ ID NO : 5
Vet775        MFNLARTAQFIYN-KEEKFTNSHYLKDTVHSLLLAEPFKIPI  596    SEQ ID NO : 6
```

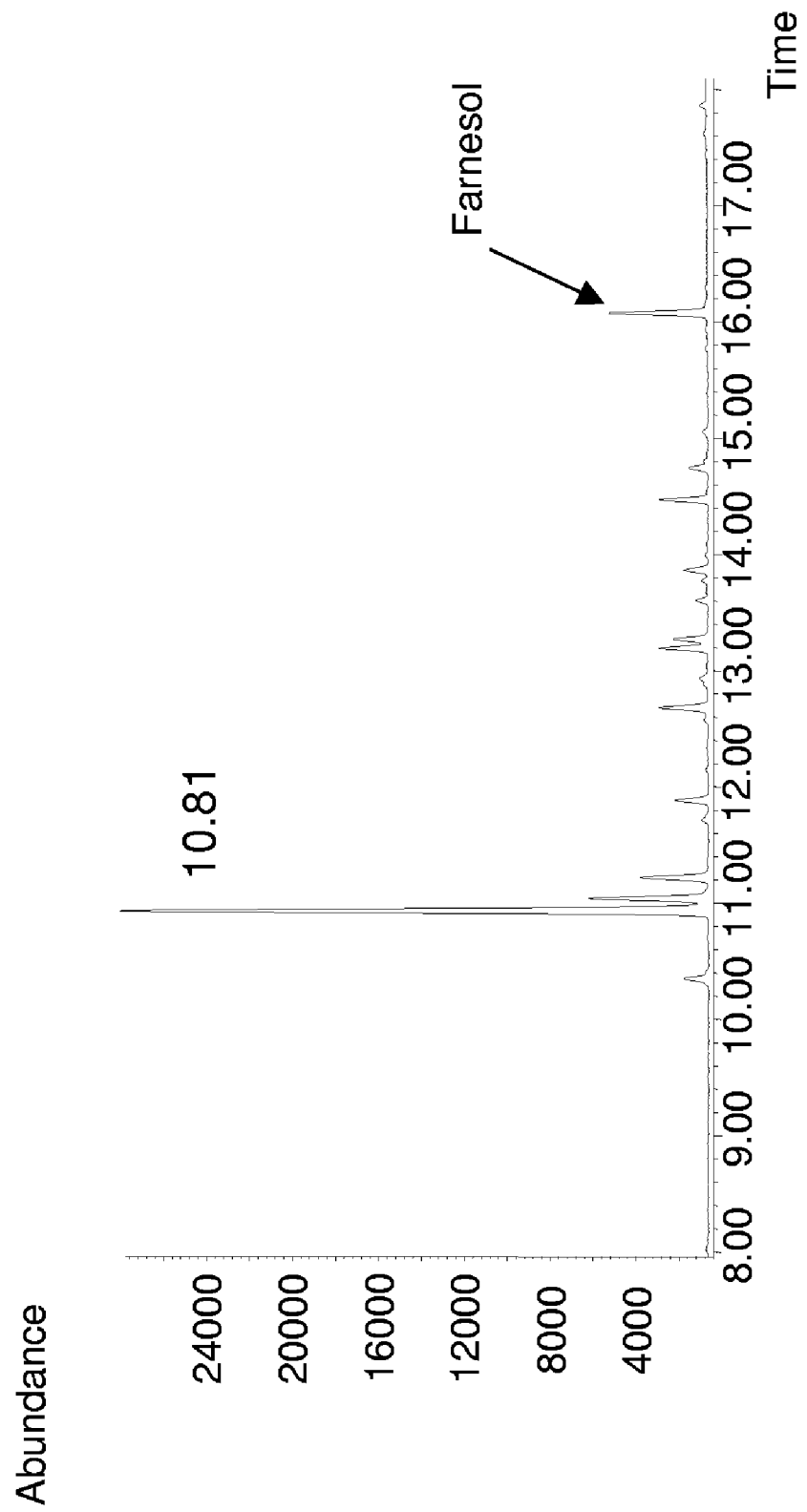
Figure 4 Part A

Figure 4 Part B
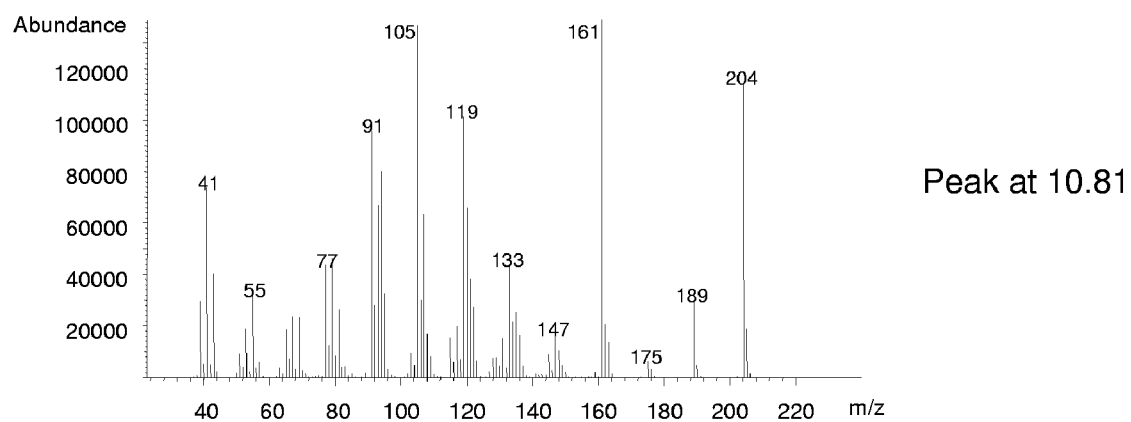
Peak at 10.81
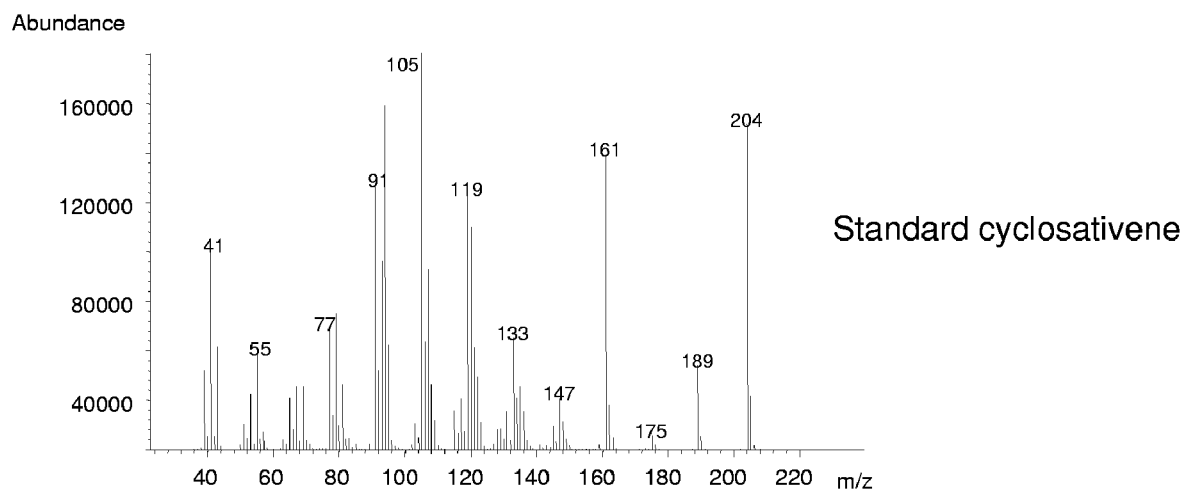
Standard cyclosativene ns a number of odorant sesquiterpe-

SEQUENCE LISTING

<160> NUMBER OF SEQ ID NOS: 72

<210> SEQ ID NO 1
<211> LENGTH: 1647
<212> TYPE: DNA
<213> ORGANISM: Vetiver zizanoides

<400> SEQUENCE: 1
atggccagca gcagtcctgt ccctctggtc acacaggtgc agcgcaagcc acagacattc    60

```
accccaagcc catggggtga cttcttcctc caccacgtcc catgcactcc atcacagttc    120
ttgtcaatga aggagagggc acagaggaag aaggaagaag tgaggcagat tatactagaa    180
aactttgcct cctccaatct ggtacggaag cttgagctcg ttgacacgct gcaacggatc    240
ggggtggact accactacaa ggaggagatc gataatttgc ttcactctat cttcgacgac    300
aaggatggag ttctgacaa tctctacatc acctcgttga ggttctattt gctcaggaag    360
catgggtatg gagtctcttc agatgtgttt gagaaattta gggatgagca agggaacatt    420
tcaagtgatg atatcagctg cttgctgatg ttgtatgatg ctgcgcatct gagaactcat    480
ggggaggaga tacttgacaa catcatcact ttcaacaaga gccatctcca atctctactg    540
ctggaaaatt tggagccaga gctacgagag gaagtgcagt gcactttgga cacctcgg     600 ttcaggcggg tcaagagagt ggaggcgagg cgctacatct ccgtatatga aagaatact    660 acacgggatg cgaccatact ggagtttgcg aaactagact acaacatctt gcaagctatc    720
tactgtgatg agttgaaaga acttacagta tggtggaagg atttccaatc acaaacagat    780
ctgagctttg cacgggacag aatggtggag ctacatttt ggatgctcgg agtggtttac    840
gagccctatt atccatattc aagaataatg atgacaaagt tcatcgtact tgcatccttg    900
ctcgatgacc tttatgacag ctatagcacc acagaggaga gcaatgcctt catcgcagcc    960
atgcaaaggt gggatgaccg aaccacagaa catcttccag catgcttgaa ggcactcttc    1020
atcaacatag taaaaaccac aaatgagatt gaggaggagt aaaacttat gaaaaataag    1080 catgctgatt tgatcaaaag actggtgatt gacactgcca aattctacca tgctgaggtt    1140
gaatggcgtg atcaacacta cataccaact gatatagaag aacatctcca aatttccacc    1200
cgtagcagtg tttgtatgca gataacaaac cttgcgctca tttcacttgg agaggtgact    1260
actaggaaag atgtcgattg ggctctcacc ttccccaaaa tcatcagagc tgcatgtatc    1320
gtggggcgcg tcggcaatga catcgtgtca cacgagcgtg aacaaacttc ggagcatgtc    1380
ggatccacgg tgcaaacttg catgaagcaa tatggggtga cagtagagga agccaatgaa    1440
aagcttagag ttataatcga agaagcatgg atggacatcg ttgaagaatg cctcgagcaa    1500
aaacgtccca tggcactttt agagacagcg gtcaacgttg caagaacaat ggatttcatg    1560
tacaagcgtg aagatgcata caccctctca ttcagcctca aggatgttat tgcttccatg    1620
tacgttaact ctgtgcgagc ttgttga                                       1647
```

<210> SEQ ID NO 2
<211> LENGTH: 1641
<212> TYPE: DNA
<213> ORGANISM: Vetiver zizanoides

<400> SEQUENCE: 2

```
atggcgcttc ctgtagcaca tcgttattcc agcgaggcag aggagctacg agaggctact     60
accttccacc caagcctatg gggcgatttc ttcctgactt accagccgcc aactgcagct    120
cagcaagcat acatggaaga acgagctgag gtattaagag aagatgttag gaagattttg    180
agggactcaa ctcaattacc agaaacactg aatcttatac tcacattgca acgacttgga    240
ctggattact actacgagaa tgagatagac aagttactgc accgtattta caactctgat    300
tacaatgata aggatctaaa cttagtttca ctgcggtttt atcttcttcg aaagaatggt    360
tacgatgtgt catcagatgt atttctaagc ttcaaaacag atgaaggggg ctttgcttat    420
ggtgacacga taagcttgtt aagcttatat aatgcagcat atttgaggag acatggagag    480
aaggtactgg atgaagcaat ttcttttact agacgtcgcc ttcaagatat cctcgaactt    540
```

-continued

```
ccagcatcac catttgcaaa ggaggtgtcc gcttcgcttc ataccctct  ttttagaagg    600 gttggaatac tagaagcaag aaattacata cctatttatg agaaagatgc tacagtgaat    660
gaagccatat tggagcttgc gaaactgaat tttaaccttc aacaacttgt tttctgtgaa    720
gagttaaagc attgcacaat gtggtggaag gagttcctag ccaaatcaaa gatgactttt    780
gttagagaca gaatagtgga ggtgtatttc tggatgaacg gggcatgcta tcaccctcca    840
tactctcatt cccgaattat acaaacaaag atcacctctt ttgttacaat aattgatgat    900
atgtttgaca catatggtac cactgaagag tgcatgaaat tgttgaagc  aattggcaga    960 tgggatgaaa gtgcagtacc tctccttcca gagtatatga agggtttcta cttatttctg   1020
ttggacacat ttcattcatt tgaggatgag ttagggccac agaagagtta tcgtgtgctt   1080
tatctaaaac atgctatgga gcgtttggtt cagcagtact acaatgaaat aaaatggcgt   1140
gatgaagact atgtgccaaa acaatgagt  gaacacctcc aagtttcaat ggaaagcatt   1200
gcatgcatcc ctattacatg tgctgcattt gttggaatgg gtgacataat aacaaaggag   1260
acactcgagt ggattttgag ctttcctcaa tttctaatgt cttttggtat atatgtacgc   1320
ctctcaaatg atgtcgcatc aaccatgcgt gaacaaacaa aagaccatag tgcctccact   1380
gtccattgtt acatgaagga acatggaaca caatgaatg atgcatgcga aaagataaaa   1440
gaacttgctg aagataaatg gaaggacatg ttagaacaat gccttgcact gacagaatta   1500
ccaaaggtca ttccacggac agtgtttgac ttcgcaagaa ccatagttaa tatgtacaag   1560
aatgatcatg atggattcac ttcttcagaa gcactcaaag aaatgataga actactattc   1620
gtgaagccag tacccaattg a                                             1641
```

<210> SEQ ID NO 3
<211> LENGTH: 1794
<212> TYPE: DNA
<213> ORGANISM: Vetiver zizanoides

<400> SEQUENCE: 3

```
atgtggaact gcagccttac tatttctgct actgctgcat cgccgccgct caggcaatgg     60
ccaggcggca tttcatggcg gcggcccagc aggttgcaat gttccgccgc aacaacacgc    120
catgacgatg accttgtcct tgacaacaaa ggcgacaacc gcctgaggga aacaccggc     180 gccgacattt tccagccatc catctgggga gatatcttcc tcggcaactc caacccagca    240
gcagcagctt catcacaaca acagcagatt cagatggaag aacgagcgga taaactcagg    300
gaagaagtgg ccaaaatgat agcaagttca acaactactg ctagtaggct gcagctcatc    360
gatgcattgg agcgtctatg cttggatcac ctgttcgaag aagagatcgg tgctgcacta    420
gcacagattg agactgctga tgtcagtgac tacgatcttg aaacggttgc cctgtggttt    480
tgtctacttc ggaaacatcg atatatggta tcaccagatg tgtttgtgag gttcaaagat    540
gaagatggag ggtttctagt gaacagtcct aaagacctac tgaacccttta caatgctgcg    600 catatgagga ctcatggaga gataatactt gaggaagccg tactattcag ccagaggcat    660
ttagaaacaa tggtaccata catggaaggg tcattggcac gtgaaataaa atctgcactt    720
gacattcccc tccctagaag acctagaatt tatgagtaca gtattacat  ctcaatgtat    780 gagaaagatg gcatggtgga tgagaaggtg ttgcaacttg caagttgaa  ctcaaacatt    840 atgcaactcc atcaccaaca tgagttgggt attgtttcaa ggtggtggaa tgatataaat    900
attgaatcaa ggcttccaca tgttcgagat agactcgtgg agtgctattt gtggatatta    960
```

```
ggggtatact acgaaccatg ttattcacga gcccgaataa tattgacaat gactactgcc    1020
atggtgaccc ttttagatga tacttatgat tcttatgcaa ctccagaaga gtgtgaatta    1080
ttcaccaagt gcattgaaag ctgggattca atgggggctc aagaccttcc cgagcgcatg    1140
aaatatggtt tggagaaaat attcgatagt tgtgagatca ttgaaaatat gctccaccaa    1200
gaggagaaat atcgcatttg gtatctaaga caatctataa aagacctggt tataagctac    1260
agcgtggagg taaaaatgct tcaagaagga tacattccaa agtccgttga ggaacatctg    1320
aagctttcac tgataaccgt tggatatccc attttggcat gtgtttcctt cgtcgggatg    1380
catgatatag caacaaagga ttgccttgat tgggtgtcca gtatacctaa aatggtggag    1440
gcactttccg tgattctcag actggtagat gacctcgagt catatgagcg agagcaactg    1500
gtccctcatg ttgcttcgac aatcgatagc tacatgaagg agcacaatgt ctccattgaa    1560
gttgcacgtg agcagatata catactcaaa gaggaatcat ggaaagattt aacaacgaa    1620 tggcttaacc cagacaataa tgtttatcca aagcagttgc tggaacggat gttcaacttg    1680
gcaaggacag cgcagttctt gtataacaaa gaagaaaaat tcacaaacag ccactatcta    1740
aaggataccg tccattcctt gttgttggcc gaaccattta agatccccat ttag           1794

<210> SEQ ID NO 4
<211> LENGTH: 548
<212> TYPE: PRT
<213> ORGANISM: Vetiver zizanoides

<400> SEQUENCE: 4

Met Ala Ser Ser Pro Val Pro Leu Val Thr Gln Val Gln Arg Lys
 1               5                  10                  15

Pro Gln Thr Phe Thr Pro Ser Pro Trp Gly Asp Phe Phe Leu His His
            20                  25                  30

Val Pro Cys Thr Pro Ser Gln Phe Leu Ser Met Lys Glu Arg Ala Gln
        35                  40                  45

Arg Lys Lys Glu Glu Val Arg Gln Ile Ile Leu Glu Asn Phe Ala Ser
    50                  55                  60

Ser Asn Leu Val Arg Lys Leu Glu Leu Val Asp Thr Leu Gln Arg Ile
65                  70                  75                  80

Gly Val Asp Tyr His Tyr Lys Glu Glu Ile Asp Asn Leu Leu His Ser
                85                  90                  95

Ile Phe Asp Asp Lys Asp Gly Gly Ser Asp Asn Leu Tyr Ile Thr Ser
            100                 105                 110

Leu Arg Phe Tyr Leu Leu Arg Lys His Gly Tyr Gly Val Ser Ser Asp
        115                 120                 125

Val Phe Glu Lys Phe Arg Asp Glu Gln Gly Asn Ile Ser Ser Asp Asp
    130                 135                 140

Ile Ser Cys Leu Leu Met Leu Tyr Asp Ala Ala His Leu Arg Thr His
145                 150                 155                 160

Gly Glu Glu Ile Leu Asp Asn Ile Ile Thr Phe Asn Lys Ser His Leu
                165                 170                 175

Gln Ser Leu Leu Leu Glu Asn Leu Glu Pro Glu Leu Arg Glu Glu Val
            180                 185                 190

Gln Cys Thr Leu Glu Thr Pro Arg Phe Arg Arg Val Lys Arg Val Glu
        195                 200                 205

Ala Arg Arg Tyr Ile Ser Val Tyr Glu Lys Asn Thr Thr Arg Asp Ala
    210                 215                 220

Thr Ile Leu Glu Phe Ala Lys Leu Asp Tyr Asn Ile Leu Gln Ala Ile
```

```
                225                 230                 235                 240
Tyr Cys Asp Glu Leu Lys Glu Leu Thr Val Trp Trp Lys Asp Phe Gln
                    245                 250                 255

Ser Gln Thr Asp Leu Ser Phe Ala Arg Asp Arg Met Val Glu Leu His
                260                 265                 270

Phe Trp Met Leu Gly Val Val Tyr Glu Pro Tyr Tyr Pro Tyr Ser Arg
            275                 280                 285

Ile Met Met Thr Lys Phe Ile Val Leu Ala Ser Leu Leu Asp Asp Leu
        290                 295                 300

Tyr Asp Ser Tyr Ser Thr Thr Glu Glu Ser Asn Ala Phe Ile Ala Ala
305                 310                 315                 320

Met Gln Arg Trp Asp Asp Arg Thr Thr Glu His Leu Pro Ala Cys Leu
                325                 330                 335

Lys Ala Leu Phe Ile Asn Ile Val Lys Thr Thr Asn Glu Ile Glu Glu
                340                 345                 350

Glu Leu Lys Leu Met Lys Asn Lys His Ala Asp Leu Ile Lys Arg Leu
            355                 360                 365

Val Ile Asp Thr Ala Lys Phe Tyr His Ala Glu Val Glu Trp Arg Asp
        370                 375                 380

Gln His Tyr Ile Pro Thr Asp Ile Glu Glu His Leu Gln Ile Ser Thr
385                 390                 395                 400

Arg Ser Ser Val Cys Met Gln Ile Thr Asn Leu Ala Leu Ile Ser Leu
                405                 410                 415

Gly Glu Val Thr Thr Arg Lys Asp Val Asp Trp Ala Leu Thr Phe Pro
            420                 425                 430

Lys Ile Ile Arg Ala Ala Cys Ile Val Gly Arg Val Gly Asn Asp Ile
        435                 440                 445

Val Ser His Glu Arg Glu Gln Thr Ser Glu His Val Gly Ser Thr Val
    450                 455                 460

Gln Thr Cys Met Lys Gln Tyr Gly Val Thr Val Glu Glu Ala Asn Glu
465                 470                 475                 480

Lys Leu Arg Val Ile Ile Glu Glu Ala Trp Met Asp Ile Val Glu Glu
                485                 490                 495

Cys Leu Glu Gln Lys Arg Pro Met Ala Leu Leu Glu Thr Ala Val Asn
            500                 505                 510

Val Ala Arg Thr Met Asp Phe Met Tyr Lys Arg Glu Asp Ala Tyr Thr
        515                 520                 525

Leu Ser Phe Ser Leu Lys Asp Val Ile Ala Ser Met Tyr Val Asn Ser
    530                 535                 540

Val Arg Ala Cys
545

<210> SEQ ID NO 5
<211> LENGTH: 546
<212> TYPE: PRT
<213> ORGANISM: Vetiver zizanoides

<400> SEQUENCE: 5

Met Ala Leu Pro Val Ala His Arg Tyr Ser Ser Glu Ala Glu Glu Leu
1               5                   10                  15

Arg Glu Ala Thr Thr Phe His Pro Ser Leu Trp Gly Asp Phe Phe Leu
                20                  25                  30

Thr Tyr Gln Pro Pro Thr Ala Ala Gln Gln Ala Tyr Met Glu Glu Arg
            35                  40                  45
```

-continued

Ala Glu Val Leu Arg Glu Asp Val Arg Lys Ile Leu Arg Asp Ser Thr
 50                  55                  60

Gln Leu Pro Glu Thr Leu Asn Leu Ile Leu Thr Leu Gln Arg Leu Gly
 65                  70                  75                  80

Leu Asp Tyr Tyr Tyr Glu Asn Glu Ile Asp Lys Leu Leu His Arg Ile
                 85                  90                  95

Tyr Asn Ser Asp Tyr Asn Asp Lys Asp Leu Asn Leu Val Ser Leu Arg
            100                 105                 110

Phe Tyr Leu Leu Arg Lys Asn Gly Tyr Asp Val Ser Ser Asp Val Phe
        115                 120                 125

Leu Ser Phe Lys Thr Asp Glu Gly Gly Phe Ala Tyr Gly Asp Thr Ile
    130                 135                 140

Ser Leu Leu Ser Leu Tyr Asn Ala Ala Tyr Leu Arg Arg His Gly Glu
145                 150                 155                 160

Lys Val Leu Asp Glu Ala Ile Ser Phe Thr Arg Arg Leu Gln Asp
                165                 170                 175

Ile Leu Glu Leu Pro Ala Ser Pro Phe Ala Lys Glu Val Ser Ala Ser
            180                 185                 190

Leu His Thr Pro Leu Phe Arg Arg Val Gly Ile Leu Glu Ala Arg Asn
        195                 200                 205

Tyr Ile Pro Ile Tyr Glu Lys Asp Ala Thr Val Asn Glu Ala Ile Leu
    210                 215                 220

Glu Leu Ala Lys Leu Asn Phe Asn Leu Gln Gln Leu Val Phe Cys Glu
225                 230                 235                 240

Glu Leu Lys His Cys Thr Met Trp Trp Lys Glu Phe Leu Ala Lys Ser
                245                 250                 255

Lys Met Thr Phe Val Arg Asp Arg Ile Val Glu Val Tyr Phe Trp Met
            260                 265                 270

Asn Gly Ala Cys Tyr His Pro Pro Tyr Ser His Ser Arg Ile Ile Gln
        275                 280                 285

Thr Lys Ile Thr Ser Phe Val Thr Ile Ile Asp Asp Met Phe Asp Thr
    290                 295                 300

Tyr Gly Thr Thr Glu Glu Cys Met Lys Phe Val Glu Ala Ile Gly Arg
305                 310                 315                 320

Trp Asp Glu Ser Ala Val Pro Leu Leu Pro Glu Tyr Met Lys Gly Phe
                325                 330                 335

Tyr Leu Phe Leu Leu Asp Thr Phe His Ser Phe Glu Asp Glu Leu Gly
            340                 345                 350

Pro Gln Lys Ser Tyr Arg Val Leu Tyr Leu Lys His Ala Met Glu Arg
        355                 360                 365

Leu Val Gln Gln Tyr Tyr Asn Glu Ile Lys Trp Arg Asp Glu Asp Tyr
    370                 375                 380

Val Pro Lys Thr Met Ser Glu His Leu Gln Val Ser Met Glu Ser Ile
385                 390                 395                 400

Ala Cys Ile Pro Ile Thr Cys Ala Ala Phe Val Gly Met Gly Asp Ile
                405                 410                 415

Ile Thr Lys Glu Thr Leu Glu Trp Ile Leu Ser Phe Pro Gln Phe Leu
            420                 425                 430

Met Ser Phe Gly Ile Tyr Val Arg Leu Ser Asn Asp Val Ala Ser Thr
        435                 440                 445

Met Arg Glu Gln Thr Lys Asp His Ser Ala Ser Thr Val His Cys Tyr
    450                 455                 460

Met Lys Glu His Gly Thr Thr Met Asn Asp Ala Cys Glu Lys Ile Lys

```
                465                 470                 475                 480
Glu Leu Ala Glu Asp Lys Trp Lys Asp Met Leu Glu Gln Cys Leu Ala
                    485                 490                 495

Leu Thr Glu Leu Pro Lys Val Ile Pro Arg Thr Val Phe Asp Phe Ala
                500                 505                 510

Arg Thr Ile Val Asn Met Tyr Lys Asn Asp His Asp Gly Phe Thr Ser
            515                 520                 525

Ser Glu Ala Leu Lys Glu Met Ile Glu Leu Leu Phe Val Lys Pro Val
        530                 535                 540

Pro Asn
545

<210> SEQ ID NO 6
<211> LENGTH: 597
<212> TYPE: PRT
<213> ORGANISM: Vetiver zizanoides

<400> SEQUENCE: 6

Met Trp Asn Cys Ser Leu Thr Ile Ser Ala Thr Ala Ala Ser Pro Pro
1               5                   10                  15

Leu Arg Gln Trp Pro Gly Gly Ile Ser Trp Arg Pro Ser Arg Leu
            20                  25                  30

Gln Cys Ser Ala Ala Thr Thr Arg His Asp Asp Leu Val Leu Asp
        35                  40                  45

Asn Lys Gly Asp Asn Arg Leu Arg Glu Asn Thr Gly Ala Asp Ile Phe
    50                  55                  60

Gln Pro Ser Ile Trp Gly Asp Ile Phe Leu Gly Asn Ser Asn Pro Ala
65                  70                  75                  80

Ala Ala Ser Ser Gln Gln Gln Ile Gln Met Glu Glu Arg Ala
            85                  90                  95

Asp Lys Leu Arg Glu Glu Val Ala Lys Met Ile Ala Ser Ser Thr Thr
            100                 105                 110

Thr Ala Ser Arg Leu Gln Leu Ile Asp Ala Leu Glu Arg Leu Cys Leu
            115                 120                 125

Asp His Leu Phe Glu Glu Ile Gly Ala Ala Leu Ala Gln Ile Glu
        130                 135                 140

Thr Ala Asp Val Ser Asp Tyr Asp Leu Glu Thr Val Ala Leu Trp Phe
145                 150                 155                 160

Cys Leu Leu Arg Lys His Arg Tyr Met Val Ser Pro Asp Val Phe Val
                165                 170                 175

Arg Phe Lys Asp Glu Asp Gly Gly Phe Leu Val Asn Ser Pro Lys Asp
            180                 185                 190

Leu Leu Asn Leu Tyr Asn Ala Ala His Met Arg Thr His Gly Glu Ile
        195                 200                 205

Ile Leu Glu Glu Ala Val Leu Phe Ser Gln Arg His Leu Glu Thr Met
    210                 215                 220

Val Pro Tyr Met Glu Gly Ser Leu Ala Arg Glu Ile Lys Ser Ala Leu
225                 230                 235                 240

Asp Ile Pro Leu Pro Arg Arg Pro Arg Ile Tyr Glu Tyr Lys Tyr Tyr
                245                 250                 255

Ile Ser Met Tyr Glu Lys Asp Gly Met Val Asp Glu Lys Val Leu Gln
            260                 265                 270

Leu Ala Lys Leu Asn Ser Asn Ile Met Gln Leu His His Gln His Glu
        275                 280                 285
```

-continued

```
Leu Gly Ile Val Ser Arg Trp Trp Asn Asp Ile Asn Ile Glu Ser Arg
    290                 295                 300

Leu Pro His Val Arg Asp Arg Leu Val Glu Cys Tyr Leu Trp Ile Leu
305                 310                 315                 320

Gly Val Tyr Tyr Glu Pro Cys Tyr Ser Arg Ala Arg Ile Ile Leu Thr
                325                 330                 335

Met Thr Thr Ala Met Val Thr Leu Leu Asp Asp Thr Tyr Asp Ser Tyr
            340                 345                 350

Ala Thr Pro Glu Glu Cys Glu Leu Phe Thr Lys Cys Ile Glu Ser Trp
        355                 360                 365

Asp Ser Met Gly Ala Gln Asp Leu Pro Glu Arg Met Lys Tyr Gly Leu
    370                 375                 380

Glu Lys Ile Phe Asp Ser Cys Glu Ile Ile Glu Asn Met Leu His Gln
385                 390                 395                 400

Glu Glu Lys Tyr Arg Ile Trp Tyr Leu Arg Gln Ser Ile Lys Asp Leu
                405                 410                 415

Val Ile Ser Tyr Ser Val Glu Val Lys Met Leu Gln Glu Gly Tyr Ile
            420                 425                 430

Pro Lys Ser Val Glu Glu His Leu Lys Leu Ser Leu Ile Thr Val Gly
        435                 440                 445

Tyr Pro Ile Leu Ala Cys Val Ser Phe Val Gly Met His Asp Ile Ala
    450                 455                 460

Thr Lys Asp Cys Leu Asp Trp Val Ser Ser Ile Pro Lys Met Val Glu
465                 470                 475                 480

Ala Leu Ser Val Ile Leu Arg Leu Val Asp Asp Leu Glu Ser Tyr Glu
                485                 490                 495

Arg Glu Gln Leu Val Pro His Val Ala Ser Thr Ile Asp Ser Tyr Met
            500                 505                 510

Lys Glu His Asn Val Ser Ile Glu Val Ala Arg Glu Gln Ile Tyr Ile
        515                 520                 525

Leu Lys Glu Glu Ser Trp Lys Asp Phe Asn Asn Glu Trp Leu Asn Pro
    530                 535                 540

Asp Asn Asn Val Tyr Pro Lys Gln Leu Leu Glu Arg Met Phe Asn Leu
545                 550                 555                 560

Ala Arg Thr Ala Gln Phe Leu Tyr Asn Lys Glu Glu Lys Phe Thr Asn
                565                 570                 575

Ser His Tyr Leu Lys Asp Thr Val His Ser Leu Leu Leu Ala Glu Pro
            580                 585                 590

Phe Lys Ile Pro Ile
        595
```

```
<210> SEQ ID NO 7
<211> LENGTH: 11
<212> TYPE: PRT
<213> ORGANISM: Vetiver zizanoides

<400> SEQUENCE: 7

Pro Ala Ala Ala Ala Ser Ser Gln Gln Gln Gln
1               5                   10

<210> SEQ ID NO 8
<211> LENGTH: 27
<212> TYPE: PRT
<213> ORGANISM: Vetiver zizanoides

<400> SEQUENCE: 8
```

Ile Val Gly Val Tyr Tyr Glu Pro Arg Tyr Ser Arg Gly Arg Ile Ile
1               5                   10                  15

Leu Lys Lys Val Leu Gly Ile Val Ser Ile Leu
                20                  25

<210> SEQ ID NO 9
<211> LENGTH: 28
<212> TYPE: PRT
<213> ORGANISM: Vetiver zizanoides

<400> SEQUENCE: 9

Met Leu Gly Val Val Tyr Glu Pro Tyr Pro Ala Tyr Ser Arg Ile
1               5                   10                  15

Met Met Thr Lys Phe Ile Val Leu Ala Ser Leu Leu
                20                  25

<210> SEQ ID NO 10
<211> LENGTH: 28
<212> TYPE: PRT
<213> ORGANISM: Vetiver zizanoides

<400> SEQUENCE: 10

Pro Ile Trp Cys Ile Met Asn Lys Ser Thr Tyr Arg Arg Ala Arg Leu
1               5                   10                  15

Ile Leu Ala Lys Ile Ile Val Leu Thr Ser Leu Leu
                20                  25

<210> SEQ ID NO 11
<211> LENGTH: 27
<212> TYPE: PRT
<213> ORGANISM: Vetiver zizanoides

<400> SEQUENCE: 11

Ala Ala Gly Gly Cys Ile Glu Pro Lys Tyr Ser Ser Phe Arg Ile Gly
1               5                   10                  15

Phe Ala Lys Phe Cys Ser Leu Ala Thr Val Met
                20                  25

<210> SEQ ID NO 12
<211> LENGTH: 27
<212> TYPE: PRT
<213> ORGANISM: Vetiver zizanoides

<400> SEQUENCE: 12

Met Asn Gly Val Cys Tyr His Pro Pro Tyr Ser His Ser Arg Ile Ile
1               5                   10                  15

Gln Thr Lys Ile Thr Ser Phe Val Thr Ile Ile
                20                  25

<210> SEQ ID NO 13
<211> LENGTH: 70
<212> TYPE: PRT
<213> ORGANISM: Vetiver zizanoides

<400> SEQUENCE: 13

Asn Leu Val Gln Ala Leu His Arg Arg Glu Leu Ala Glu Val Thr Arg
1               5                   10                  15

Trp Trp Lys Glu Ser Arg Leu Gly Glu Gly Asp Val Asp Tyr Ser Phe
                20                  25                  30

Ala Arg Asp Arg Val Val Glu Cys Phe Phe Cys Ala Ala Cys Ile Ala
                35                  40                  45

-continued

Pro Glu Pro Arg Leu Ala Asp Cys Arg Glu Val Leu Ala Lys Thr Gly
    50                  55                  60

Ala Leu Ile Val His Leu
 65                  70

<210> SEQ ID NO 14
<211> LENGTH: 57
<212> TYPE: PRT
<213> ORGANISM: Vetiver zizanoides

<400> SEQUENCE: 14

Thr Asn Ser Ile Phe Arg Trp Trp Arg Thr Leu Tyr Lys Asp Val Lys
1               5                   10                  15

Leu Ser Tyr Cys Arg Asp Arg Leu Val Glu Met Tyr Phe Trp Thr Ile
            20                  25                  30

Glu Met Leu Pro Trp Glu Glu Cys Ser Arg Ser Arg Ile Val Leu Thr
        35                  40                  45

Lys Val Ile Ala Phe Ala Thr Leu Met
    50                  55

<210> SEQ ID NO 15
<211> LENGTH: 29
<212> TYPE: DNA
<213> ORGANISM: Artificial
<220> FEATURE:
<223> OTHER INFORMATION: Primer Tps_monocot_F1
<220> FEATURE:
<221> NAME/KEY: misc_feature
<222> LOCATION: (27)..(27)
<223> OTHER INFORMATION: a or g or c or t

<400> SEQUENCE: 15
cggttctacc tgctgcggma rmabggnta                                      29

<210> SEQ ID NO 16
<211> LENGTH: 28
<212> TYPE: DNA
<213> ORGANISM: Artificial
<220> FEATURE:
<223> OTHER INFORMATION: Primer Tps_monocot_F2
<220> FEATURE:
<221> NAME/KEY: misc_feature
<222> LOCATION: (20)..(20)
<223> OTHER INFORMATION: a or g or c or t
<220> FEATURE:
<221> NAME/KEY: misc_feature
<222> LOCATION: (26)..(26)
<223> OTHER INFORMATION: a or g or c or t

<400> SEQUENCE: 16
ccaggtccct gctgaccytn tayrangc                                       28

<210> SEQ ID NO 17
<211> LENGTH: 30
<212> TYPE: DNA
<213> ORGANISM: Artificial
<220> FEATURE:
<223> OTHER INFORMATION: Primer_Tps_monocot_F3
<220> FEATURE:
<221> NAME/KEY: misc_feature
<222> LOCATION: (24)..(24)
<223> OTHER INFORMATION: a or g or c or t

<400> SEQUENCE: 17
gccgtgctgg agctggccaa rytnraytty                                     30

```
<210> SEQ ID NO 18
<211> LENGTH: 30
<212> TYPE: DNA
<213> ORGANISM: Artificial
<220> FEATURE:
<223> OTHER INFORMATION: Primer Tps_monocot_F4
<220> FEATURE:
<221> NAME/KEY: misc_feature
<222> LOCATION: (21)..(21)
<223> OTHER INFORMATION: a or g or c or t

<400> SEQUENCE: 18
cgggaccgga tcgtggagrh nyayttytgg                                    30

<210> SEQ ID NO 19
<211> LENGTH: 30
<212> TYPE: DNA
<213> ORGANISM: Artificial
<220> FEATURE:
<223> OTHER INFORMATION: Primer Tps_monocot_R1
<220> FEATURE:
<221> NAME/KEY: misc_feature
<222> LOCATION: (9)..(9)
<223> OTHER INFORMATION: a or g or c or t

<400> SEQUENCE: 19
ctrctrwana wrctgtgggt gccgtggtgg                                    30

<210> SEQ ID NO 20
<211> LENGTH: 30
<212> TYPE: DNA
<213> ORGANISM: Artificial
<220> FEATURE:
<223> OTHER INFORMATION: Primer Tps_monocot_R2
<220> FEATURE:
<221> NAME/KEY: misc_feature
<222> LOCATION: (9)..(9)
<223> OTHER INFORMATION: a or g or c or t

<400> SEQUENCE: 20
ctrctrtrna wrctgtgggt gccgtggtgg                                    30

<210> SEQ ID NO 21
<211> LENGTH: 18
<212> TYPE: DNA
<213> ORGANISM: Artificial
<220> FEATURE:
<223> OTHER INFORMATION: Primer TpsVF1

<400> SEQUENCE: 21
hhvthwcmmg gtggtgga                                                 18

<210> SEQ ID NO 22
<211> LENGTH: 18
<212> TYPE: DNA
<213> ORGANISM: Artificial
<220> FEATURE:
<223> OTHER INFORMATION: Primer TpsVF2
<220> FEATURE:
<221> NAME/KEY: misc_feature
<222> LOCATION: (3)..(3)
<223> OTHER INFORMATION: a or c or g or t

<400> SEQUENCE: 22
gtngarkbbt atktttgg                                                 18

<210> SEQ ID NO 23
<211> LENGTH: 25
<212> TYPE: DNA
```

<210> SEQ ID NO 23
<211> LENGTH: 25
<212> TYPE: DNA
<213> ORGANISM: Artificial
<220> FEATURE:
<223> OTHER INFORMATION: Primer TpsCF1

<400> SEQUENCE: 23
gckaagwtvg gkttcaathw kbtdc                                              25

<210> SEQ ID NO 24
<211> LENGTH: 29
<212> TYPE: DNA
<213> ORGANISM: Artificial
<220> FEATURE:
<223> OTHER INFORMATION: Primer TpsCF2
<220> FEATURE:
<221> NAME/KEY: misc_feature
<222> LOCATION: (9)..(9)
<223> OTHER INFORMATION: a or c or g or t

<400> SEQUENCE: 24
gggawwgwnw bgttgaakkt tattttttgg                                         29

<210> SEQ ID NO 25
<211> LENGTH: 22
<212> TYPE: DNA
<213> ORGANISM: Artificial
<220> FEATURE:
<223> OTHER INFORMATION: Primer TpsVR3

<400> SEQUENCE: 25
crtrmktrtc gwadgkgtcr tc                                                 22

<210> SEQ ID NO 26
<211> LENGTH: 26
<212> TYPE: DNA
<213> ORGANISM: Artificial
<220> FEATURE:
<223> OTHER INFORMATION: Primer TpsCR3
<220> FEATURE:
<221> NAME/KEY: misc_feature
<222> LOCATION: (9)..(9)
<223> OTHER INFORMATION: a or c or g or t

<400> SEQUENCE: 26
gtwscgtgng hgtcgtahgk gtcatc                                             26

<210> SEQ ID NO 27
<211> LENGTH: 32
<212> TYPE: DNA
<213> ORGANISM: Artificial
<220> FEATURE:
<223> OTHER INFORMATION: Primer CA711_F1

<400> SEQUENCE: 27
ctcacgagga cgaataatat tgaagaaggt cc                                      32

<210> SEQ ID NO 28
<211> LENGTH: 28
<212> TYPE: DNA
<213> ORGANISM: Artificial
<220> FEATURE:
<223> OTHER INFORMATION: Primer CA711_F2

<400> SEQUENCE: 28
attgaagaag gtccttggca ttgtttcc                                           28

<210> SEQ ID NO 29
<211> LENGTH: 30

```
<212> TYPE: DNA
<213> ORGANISM: Artificial
<220> FEATURE:
<223> OTHER INFORMATION: Primer CA717_F1

<400> SEQUENCE: 29
gctcggagtg gtttacgagc cctattatcc                                        30

<210> SEQ ID NO 30
<211> LENGTH: 32
<212> TYPE: DNA
<213> ORGANISM: Artificial
<220> FEATURE:
<223> OTHER INFORMATION: Primer CA717_F2

<400> SEQUENCE: 30
gatgacaaag ttcatcgtac ttgcatcctt gc                                     32

<210> SEQ ID NO 31
<211> LENGTH: 19
<212> TYPE: DNA
<213> ORGANISM: Artificial
<220> FEATURE:
<223> OTHER INFORMATION: Primer CA725_F1

<400> SEQUENCE: 31
ctgcgccgcc tgcatcgcg                                                    19

<210> SEQ ID NO 32
<211> LENGTH: 23
<212> TYPE: DNA
<213> ORGANISM: Artificial
<220> FEATURE:
<223> OTHER INFORMATION: Primer CA725_F2

<400> SEQUENCE: 32
gcgcctggcg gactgcaggg agg                                               23

<210> SEQ ID NO 33
<211> LENGTH: 25
<212> TYPE: DNA
<213> ORGANISM: Artificial
<220> FEATURE:
<223> OTHER INFORMATION: Primer CA731_F1

<400> SEQUENCE: 33
ccctgggagg agtgctctcg ttcac                                             25

<210> SEQ ID NO 34
<211> LENGTH: 32
<212> TYPE: DNA
<213> ORGANISM: Artificial
<220> FEATURE:
<223> OTHER INFORMATION: Primer CA731_F2

<400> SEQUENCE: 34
ggatagttct caccaaagtt attgcatttg cg                                     32

<210> SEQ ID NO 35
<211> LENGTH: 26
<212> TYPE: DNA
<213> ORGANISM: Artificial
<220> FEATURE:
<223> OTHER INFORMATION: Primer CA733_F1

<400> SEQUENCE: 35
```

```
atgaacgggg tatgctatca ccctcc                                          26

<210> SEQ ID NO 36
<211> LENGTH: 23
<212> TYPE: DNA
<213> ORGANISM: Artificial
<220> FEATURE:
<223> OTHER INFORMATION: Primer CA733_F2

<400> SEQUENCE: 36
caccctccat actctcattc ccg                                             23

<210> SEQ ID NO 37
<211> LENGTH: 23
<212> TYPE: DNA
<213> ORGANISM: Artificial
<220> FEATURE:
<223> OTHER INFORMATION: Primer CA775_R

<400> SEQUENCE: 37
ggtggagcat attttcaatg atc                                             23

<210> SEQ ID NO 38
<211> LENGTH: 22
<212> TYPE: DNA
<213> ORGANISM: Artificial
<220> FEATURE:
<223> OTHER INFORMATION: Primer CA775_R1

<400> SEQUENCE: 38
atgcacccgg gaaggtcttg ag                                              22

<210> SEQ ID NO 39
<211> LENGTH: 25
<212> TYPE: DNA
<213> ORGANISM: Artificial
<220> FEATURE:
<223> OTHER INFORMATION: Primer CA775_R2

<400> SEQUENCE: 39
gaatcccagc tttcaatgca cttgg                                           25

<210> SEQ ID NO 40
<211> LENGTH: 23
<212> TYPE: DNA
<213> ORGANISM: Artificial
<220> FEATURE:
<223> OTHER INFORMATION: Primer CA717_R

<400> SEQUENCE: 40
ctcctcctca atctcatttg tgg                                             23

<210> SEQ ID NO 41
<211> LENGTH: 25
<212> TYPE: DNA
<213> ORGANISM: Artificial
<220> FEATURE:
<223> OTHER INFORMATION: Primer CA717_R1

<400> SEQUENCE: 41
gtgccttcaa gcatgctgga agatg                                           25

<210> SEQ ID NO 42
<211> LENGTH: 24
<212> TYPE: DNA
<213> ORGANISM: Artificial
```

-continued

```
<220> FEATURE:
<223> OTHER INFORMATION: Primer CA717_R2

<400> SEQUENCE: 42
gtggttcggt catcccacct ttgc                                              24

<210> SEQ ID NO 43
<211> LENGTH: 27
<212> TYPE: DNA
<213> ORGANISM: Artificial
<220> FEATURE:
<223> OTHER INFORMATION: Primer CA782_F1

<400> SEQUENCE: 43
ccaatattgg tgtattatga acaagag                                           27

<210> SEQ ID NO 44
<211> LENGTH: 22
<212> TYPE: DNA
<213> ORGANISM: Artificial
<220> FEATURE:
<223> OTHER INFORMATION: Primer CA782_F2

<400> SEQUENCE: 44
caggcgtgca cgactgatcc tc                                                22

<210> SEQ ID NO 45
<211> LENGTH: 20
<212> TYPE: DNA
<213> ORGANISM: Artificial
<220> FEATURE:
<223> OTHER INFORMATION: Primer CA783_F1

<400> SEQUENCE: 45
gcagcaggag gatgtagaac                                                   20

<210> SEQ ID NO 46
<211> LENGTH: 31
<212> TYPE: DNA
<213> ORGANISM: Artificial
<220> FEATURE:
<223> OTHER INFORMATION: Primer CA783_F2

<400> SEQUENCE: 46
ccaaatattc ttcttttaga attggctttg c                                      31

<210> SEQ ID NO 47
<211> LENGTH: 31
<212> TYPE: DNA
<213> ORGANISM: Artificial
<220> FEATURE:
<223> OTHER INFORMATION: Primer CA783_F3

<400> SEQUENCE: 47
gaattggctt tgcaaaattt tgttctcttg c                                      31

<210> SEQ ID NO 48
<211> LENGTH: 24
<212> TYPE: DNA
<213> ORGANISM: Artificial
<220> FEATURE:
<223> OTHER INFORMATION: Primer CA775_RB

<400> SEQUENCE: 48
cctcacaaac acatctggtg atac                                              24
```

<210> SEQ ID NO 49
<211> LENGTH: 21
<212> TYPE: DNA
<213> ORGANISM: Artificial
<220> FEATURE:
<223> OTHER INFORMATION: Primer CA775_R1B

<400> SEQUENCE: 49
cagggcaacc gtttcaagat c                                    21

<210> SEQ ID NO 50
<211> LENGTH: 28
<212> TYPE: DNA
<213> ORGANISM: Artificial
<220> FEATURE:
<223> OTHER INFORMATION: Primer CA775_R2B

<400> SEQUENCE: 50
cactgacatc agcagtctca atctgtgc                             28

<210> SEQ ID NO 51
<211> LENGTH: 22
<212> TYPE: DNA
<213> ORGANISM: Artificial
<220> FEATURE:
<223> OTHER INFORMATION: Primer CA733_R

<400> SEQUENCE: 51
gaaggagagg tactgcactt tc                                   22

<210> SEQ ID NO 52
<211> LENGTH: 19
<212> TYPE: DNA
<213> ORGANISM: Artificial
<220> FEATURE:
<223> OTHER INFORMATION: Primer CA733_R1

<400> SEQUENCE: 52
cccatctgcc aattgcttc                                       19

<210> SEQ ID NO 53
<211> LENGTH: 30
<212> TYPE: DNA
<213> ORGANISM: Artificial
<220> FEATURE:
<223> OTHER INFORMATION: Primer CA733_R2

<400> SEQUENCE: 53
catgcactct tcagtggtac catatgtgtc                           30

<210> SEQ ID NO 54
<211> LENGTH: 27
<212> TYPE: DNA
<213> ORGANISM: Artificial
<220> FEATURE:
<223> OTHER INFORMATION: Primer CA775_R1_marath

<400> SEQUENCE: 54
ggtgatccaa gcatagacgc tccaatg                              27

<210> SEQ ID NO 55
<211> LENGTH: 30
<212> TYPE: DNA
<213> ORGANISM: Artificial
<220> FEATURE:
<223> OTHER INFORMATION: Primer CA775_R2_marath

```
<400> SEQUENCE: 55
cgatgagctg cagcctacta gcagtagttg                                    30

<210> SEQ ID NO 56
<211> LENGTH: 36
<212> TYPE: DNA
<213> ORGANISM: Artificial
<220> FEATURE:
<223> OTHER INFORMATION: Primer dTadaptor

<400> SEQUENCE: 56
aattcggtac ccgggatcct tttttttttt tttttt                             36

<210> SEQ ID NO 57
<211> LENGTH: 18
<212> TYPE: DNA
<213> ORGANISM: Artificial
<220> FEATURE:
<223> OTHER INFORMATION: Primer adaptorP

<400> SEQUENCE: 57
aatcggtacc cgggatcc                                                 18

<210> SEQ ID NO 58
<211> LENGTH: 31
<212> TYPE: DNA
<213> ORGANISM: Artificial
<220> FEATURE:
<223> OTHER INFORMATION: Primer CA717_Nde

<400> SEQUENCE: 58
tactgacata tggccagcag cagtcctgtc c                                  31

<210> SEQ ID NO 59
<211> LENGTH: 39
<212> TYPE: DNA
<213> ORGANISM: Artificial
<220> FEATURE:
<223> OTHER INFORMATION: Primer CA717_Kpn

<400> SEQUENCE: 59
ttggtacctc aacaagctcg cacagagtta acgtacatg                          39

<210> SEQ ID NO 60
<211> LENGTH: 36
<212> TYPE: DNA
<213> ORGANISM: Artificial
<220> FEATURE:
<223> OTHER INFORMATION: Primer 733_Nco

<400> SEQUENCE: 60
ctagccatgg cgcttcctgt agcacatcgt tattcc                             36

<210> SEQ ID NO 61
<211> LENGTH: 39
<212> TYPE: DNA
<213> ORGANISM: Artificial
<220> FEATURE:
<223> OTHER INFORMATION: Primer 733_Eco

<400> SEQUENCE: 61
cggaattcaa ttgggtactg gcttcacgaa tagtagttc                          39

<210> SEQ ID NO 62
```

-continued

<210> SEQ ID NO 62
<211> LENGTH: 39
<212> TYPE: DNA
<213> ORGANISM: Artificial
<220> FEATURE:
<223> OTHER INFORMATION: Primer 775_fus1-f

<400> SEQUENCE: 62 cacccccaagc ccatggggag atatcttcct cggcaactc                                    39

<210> SEQ ID NO 63
<211> LENGTH: 37
<212> TYPE: DNA
<213> ORGANISM: Artificial
<220> FEATURE:
<223> OTHER INFORMATION: Primer 775_fus1-r

<400> SEQUENCE: 63
ggaagatatc tccccatggg cttggggtga atgtctg                                       37

<210> SEQ ID NO 64
<211> LENGTH: 40
<212> TYPE: DNA
<213> ORGANISM: Artificial
<220> FEATURE:
<223> OTHER INFORMATION: Primer 775_fus2-f

<400> SEQUENCE: 64
gctcgttctt ccattgacaa gaactgtgat ggagtgcatg                                    40

<210> SEQ ID NO 65
<211> LENGTH: 41
<212> TYPE: DNA
<213> ORGANISM: Artificial
<220> FEATURE:
<223> OTHER INFORMATION: Primer 775_fus2-r

<400> SEQUENCE: 65
cacagttctt gtcaatggaa gaacgagcgg ataaactcag g                                  41

<210> SEQ ID NO 66
<211> LENGTH: 33
<212> TYPE: DNA
<213> ORGANISM: Artificial
<220> FEATURE:
<223> OTHER INFORMATION: Primer 775_fus_Nco

<400> SEQUENCE: 66
ctagccatgg ccagcagcag tcctgctcct ctg                                           33

<210> SEQ ID NO 67
<211> LENGTH: 34
<212> TYPE: DNA
<213> ORGANISM: Artificial
<220> FEATURE:
<223> OTHER INFORMATION: Primer 775_fus_Eco

<400> SEQUENCE: 67
cggaattcaa atggggatct taaatggttc ggcc                                          34

<210> SEQ ID NO 68
<211> LENGTH: 32
<212> TYPE: DNA
<213> ORGANISM: Artificial
<220> FEATURE:
<223> OTHER INFORMATION: Primer 775_mut_F2

<400> SEQUENCE: 68

```
gacaatgact actgcaatgg tgacccttt ag                                  32

<210> SEQ ID NO 69
<211> LENGTH: 32
<212> TYPE: DNA
<213> ORGANISM: Artificial
<220> FEATURE:
<223> OTHER INFORMATION: Primer 775_mut_R2

<400> SEQUENCE: 69
ctaaaagggt caccattgca gtagtcattg tc                                 32

<210> SEQ ID NO 70
<211> LENGTH: 25
<212> TYPE: DNA
<213> ORGANISM: Artificial
<220> FEATURE:
<223> OTHER INFORMATION: Primer 775_mut1F

<400> SEQUENCE: 70
caccccaagc ccttggggag atatc                                         25

<210> SEQ ID NO 71
<211> LENGTH: 25
<212> TYPE: DNA
<213> ORGANISM: Artificial
<220> FEATURE:
<223> OTHER INFORMATION: Primer 775_mut1R

<400> SEQUENCE: 71
gatatctccc caagggcttg gggtg                                         25

<210> SEQ ID NO 72
<211> LENGTH: 39
<212> TYPE: DNA
<213> ORGANISM: Artificial
<220> FEATURE:
<223> OTHER INFORMATION: Primer Vet775_Nco

<400> SEQUENCE: 72
ctagccatgg cgaactgcag ccttactatt tctgctact                          39
```

SESQUITERPENE SYNTHASES AND METHODS OF THEIR USE

TECHNICAL FIELD

The present invention relates to novel terpene synthases. The invention further relates to nucleic acids encoding terpene synthases, to methods for preparing variant terpene synthases, and to host-organisms expressing the polypeptides of the invention. The present invention further comprises methods for making a terpene synthase and methods for making terpenoids.

TECHNICAL BACKGROUND AND PROBLEMS TO BE SOLVED

Terpenoids or terpenes represent a family of natural products found in most organisms (bacteria, fungi, animal, plants). Terpenoids are made up of five carbon units called isoprene units. They can be classified by the number of isoprene units present in their structure: monoterpenes (C10), sesquiterpenes (C15), diterpenes (C20), triterpenes (C30), tetraterpenes (C40) and polyterpenes (Cn, $n \geq 45$). The plant kingdom contains the highest diversity of monoterpenes and sesquiterpenes.

The monoterpenes and sesquiterpenes are the most structurally diverse isoprenoids. They are usually volatile compounds and are mostly found in plants were they play a role in defense against pathogens and herbivores attacks, in pollinator attraction and in plant-plant communication.

Some plants, known as aromatic plants or essential-oil-plants, accumulate large amounts of monoterpenes and sesquiterpenes in their leaves, roots or stems. Classical examples of such plants are members from the plant families Lamiaceae, Rutaceae, Solanaceae, and Poaceae, for example.

Monoterpene and sesquiterpene accumulating plants have been of interest for thousands of years because of their flavor and fragrance properties and their cosmetic, medicinal and anti-microbial effects. The terpenes accumulated in the plants can be extracted by different means such as steam distillation that produces the so-called essential oil containing the concentrated terpenes. Such natural plant extracts are important components for the flavor and perfumery industry.

Many sesquiterpene compounds are used in perfumery. For example, Vetiver oil, extracted from the roots of *Vetiver zizanoides*, is known to contain a number of odorant sesquiterpenes, amongst which α-vetivone, β-vetivone and zizanoic acid, are the most characteristic. *Vetiver zizanoides* is currently cultivated in Reunion, the Philippines, Comoro Islands, Japan, West Africa and South America.

Generally, the price and availability of plant natural extracts such as Vetiver oil is dependent on the abundance, the oil yield and the geographical origin of the plants. In some years, the availability of commercially available natural extracts decreases, going hand in hand with a worsening of their quality. Under these circumstances, the use of these ingredients in high quality perfumery products is no longer possible.

Therefore, it would be an advantage to provide a source of sesquiterpenes, which is less subjected to fluctuations in availability and quality. Chemical synthesis would seem to be an evident option for the preparation of sesquiterpenes, however, these compounds generally have a highly complex structure and so far no economic synthetic process for the preparation of sesquiterpenes has been developed.

It is therefore an objective of the present invention to provide ways of producing a high quality of sesquiterpenes in an economic and reliable way.

The biosynthesis of terpenes in plants has been extensively studied and is not further detailed in here, but reference is made to Dewick P, *Nat. Prod. Rep.*, 2002, 19, 181-222, which reviews the state of the art of terpene biosynthetic pathways.

The sesquiterpene synthases convert FPP to the different sesquiterpene skeletons. Over 300 sesquiterpene hydrocarbons and 3000 sesquiterpenoids have been identified (Joulain, D., and König, W. A. The Atlas of Spectral Data of Sesquiterpene Hydrocarbons, EB Verlag, Hamburg, 1998; Connolly, J. D., Hill R. A. Dictionary of Terpenoids, Vol 1, Chapman and Hall (publisher), 1991), and many new structures are identified each year. There is virtually an infinity of sesquiterpene synthases present in the plant kingdom, all using the same substrate but having different product profiles.

A cDNA encoding a trans-α-bisabolene synthase has been reported by Bohlmann, J, Crock, J., Jetter, R., and Croteau R. (1998) Terpenoid-based defenses in conifers: cDNA cloning, characterization, and functional expression of wound-inducible (E)-α-bisabolene synthase from grand fir (*Abies grandis*). *Proc. Natl. Acad. Sci. USA* 95, 6756-6761. However, this enzyme catalyses one cyclation step and produces almost exclusively the bisabolene sesquiterpene.

Köllner T et al (2004) The plant cell 16(5), 1115-1131, disclose a number of putative terpene synthase genes isolated from *Zea mays*, most of which did not encode functional enzymes. DNA sequences of functional synthases, Tps4-B73 and Tps5-1 delprim are available under accession number AY518310 and AY518313. Bergamotene was only a minor product produced by the encoded enzymes, representing maximally 2.6 wt. % of the total sesquiterpenes produced.

Despite extensive chemical studies of terpene cyclisation, the isolation of the enzymes is difficult, particularly in plants, due to their low abundance, often transient expression patterns, and complexity of purifying them from the mixtures of resins and phenolic compounds in tissues where they are expressed.

In view of the above, the objective of the present invention is to provide new terpene synthases. Another objective is to isolate terpene synthases from the plant *Vetiveria zizanoides*. It is an objective of the present invention to provide terpene syntases capable of synthetizing terpenes for the synthesis of which so far no enzyme has been reported.

In particular, it is an objective to provide enzymes capable of synthesising substantial amounts of sesquiterpenes having a santalene or bergamotene carbon skeleton. There is no report of the genetic basis underlying a santalene synthase, and bergamotane is synthesised only in trace amounts by known terpene synthases.

In the same line, it is an objective to provide methods for making terpenoids in an economic way, as indicated above. Accordingly, the present invention has the objective to produce sesquiterpenes while having little waste, a more energy and resource efficient process and while reducing dependency on fossil fuels. It is a further objective to provide enzymes capable of synthesizing terpenoids, which are useful as perfumery and/or aroma ingredients.

SUMMARY OF THE INVENTION

Remarkably, the present inventors cloned cDNAs encoding novel sesquiterpenes in roots of *Vetiver zitanoides*. Surprisingly, the novel sesquiterpene synthases were capable of synthetising sesquiterpenes, which have so far not been isolated from *Vetiver*, such as cyclocopacamphene, (+)-epi-β- santalene, trans-α-bergamotene, cis-α-bergamotene, β-bisabolene, and/or trans-γ-bisabolene. Therefore, the present invention provides the first cloned sesquiterpene synthases able to catalyse the cyclisation of FPP to the bisabolyl cation and subsequent cyclization to the bergamotane and santalane skeleton. For the first time, a terpene cyclase capable of synthesizing substantial amounts of bi-cyclic derivatives of the bisabolyl cation is reported.

Accordingly, the present invention provides, in a first aspect, An isolated nucleic acid selected from:
(a) a nucleic acid comprising a nucleotide sequence having at least 82.4% identity with SEQ ID NO: 2;
(b) a nucleic acid comprising a nucleotide sequence encoding a polypeptide having at least 76.8% sequence identity with SEQ ID NO: 5;
(c) a nucleic acid comprising a nucleotide sequence that hybridises to the nucleotide sequence SEQ ID NO: 2 under moderate stringency conditions;
(d) a nucleic acid comprising a nucleotide sequence encoding a polypeptide capable of synthesising a bi-cyclic and/or tri-cyclic sesquiterpene comprising a $C_3$-$C_7$ bond; and/or,
(e) a nucleic acid comprising a nucleotide sequence encoding a polypeptide capable of synthesising at least one bergamotene and, optionally, other sesquiterpenes, characterized in that begamotenes constitute at least 10 wt. % of the total of sesquiterpene products synthesised by the polypeptide;
wherein the polypeptide encoded by any of the said nucleic acids of (a)-(e) has terpene synthase activity.

In a further aspect, the present invention provides an isolated nucleic acid selected from:
(a) a nucleic acid comprising a nucleotide sequence having at least 59% sequence identity with SEQ ID NO: 1;
(b) a nucleic acid comprising a nucleotide sequence encoding a polypeptide having at least 50% of amino acid sequence identity with SEQ ID NO: 4;
(c) a nucleic acid that hybridises to SEQ ID NO: 1 under moderate stringency conditions;
(d) a nucleic acid comprising a nucleotide sequence encoding a polypeptide capable of synthesising cyclocopacamphene;

wherein the polypeptide encoded by said nucleic acid has terpene synthase activity.

In a further aspect, the present invention provides an isolated polypeptide selected from:
(a) a polypeptide comprising an amino acid sequence having at least 76.8% of amino acid sequence identity with SEQ ID NO: 5;
(b) a polypeptide capable of synthesising a bi-cyclic and/or tri-cyclic sesquiterpene comprising a $C_3$-$C_7$ bond;
(c) a polypeptide capable of synthesising at least one bergamotene and, optionally, other sesquiterpenes, characterized in that begamotenes constitute at least 10 wt. % of the total of sesquiterpene products synthesised by the polypeptide.

In a still further aspect, the present invention provides a polypeptide selected from:
(a) a polypeptide comprising an amino acid sequence having at least 76.8% of amino acid sequence identity with SEQ ID NO: 5;
(b) a polypeptide capable of synthesising a bi-cyclic and/or tri-cyclic sesquiterpene comprising a $C_3$-$C_7$ bond;
(c) a polypeptide capable of synthesising at least one bergamotene and, optionally, other sesquiterpenes, characterized in that begamotenes constitute at least 5 wt. % of the total of sesquiterpene products synthesised by the polypeptide.

The present invention further relates to methods for preparing a variant polypeptide having terpene synthase activity, as set out in the claims and the detailed description.

In further aspects, the present invention provides vectors and host organisms or cells comprising any of the nucleic acids of the invention.

In a still further aspects, the present invention provides different methods of making a terpene synthase, and, in addition, methods of making terpenoids, for example sesquiterpenes, as set out in the claims and the detailed description.

In the figures,

FIG. 1 shows the structure of sesquiterpene compounds synthesized by the terpene synthases of the present invention, sesquiterpene compounds isolated from Vetiver oil and other sesquiterpene compounds discussed in the text, in particular (1) cis-alpha-bergamotene, (2) trans-alpha-bergamotene, (3) epi-beta-santalene, (4) beta-bisabolene, (5) trans-gamma-bisabolene, (6) cyclosativene and (7) cyclocopacamphene. Sesquiterpene compounds previously reported from Vetiver oil are (8) zizanoic acid, (9) alpha-vetivone, (10) beta-vetivone, (11) isobisabolene, (12) beta-bisabolol, (13) dehydrocurcumene, (14) (Z)-trans-alpha-bergamotol, and (15) (Z)-(+)-epi-beta-santalol.

FIG. 2 shows the alignment of amino acid sequences deduced form the fragments of cDNAs encoding for sesquiterpene synthases obtained by RT-PCR (SEQ ID NO: 8-14).

FIG. 3 shows a comparison of the full length amino acid sequences SEQ ID NO: 4, SEQ ID NO: 5, and SEQ ID NO: 6 of the present invention. Identical amino acids are shown against a black background, amino acids having similar ionic charge are shown against a grey background, and unrelated amino acids are shown against a white background.

FIG. 4 shows in part A) a gas chromatogram (GC) of sesquiterpenes obtained from an enzymatic assay in which FFP was exposed to a polypeptide having an amino acid sequence substantially as set out in SEQ ID NO: 4. In part B), FIG. 4 shows a mass spectre (MS) of the major peak (10.81) of part A), which is compared to the corresponding spectre of standard cyclosativene, thus indicating the nature of the sesquiterpene obtained in the enzymatic assay.

Figure 1:
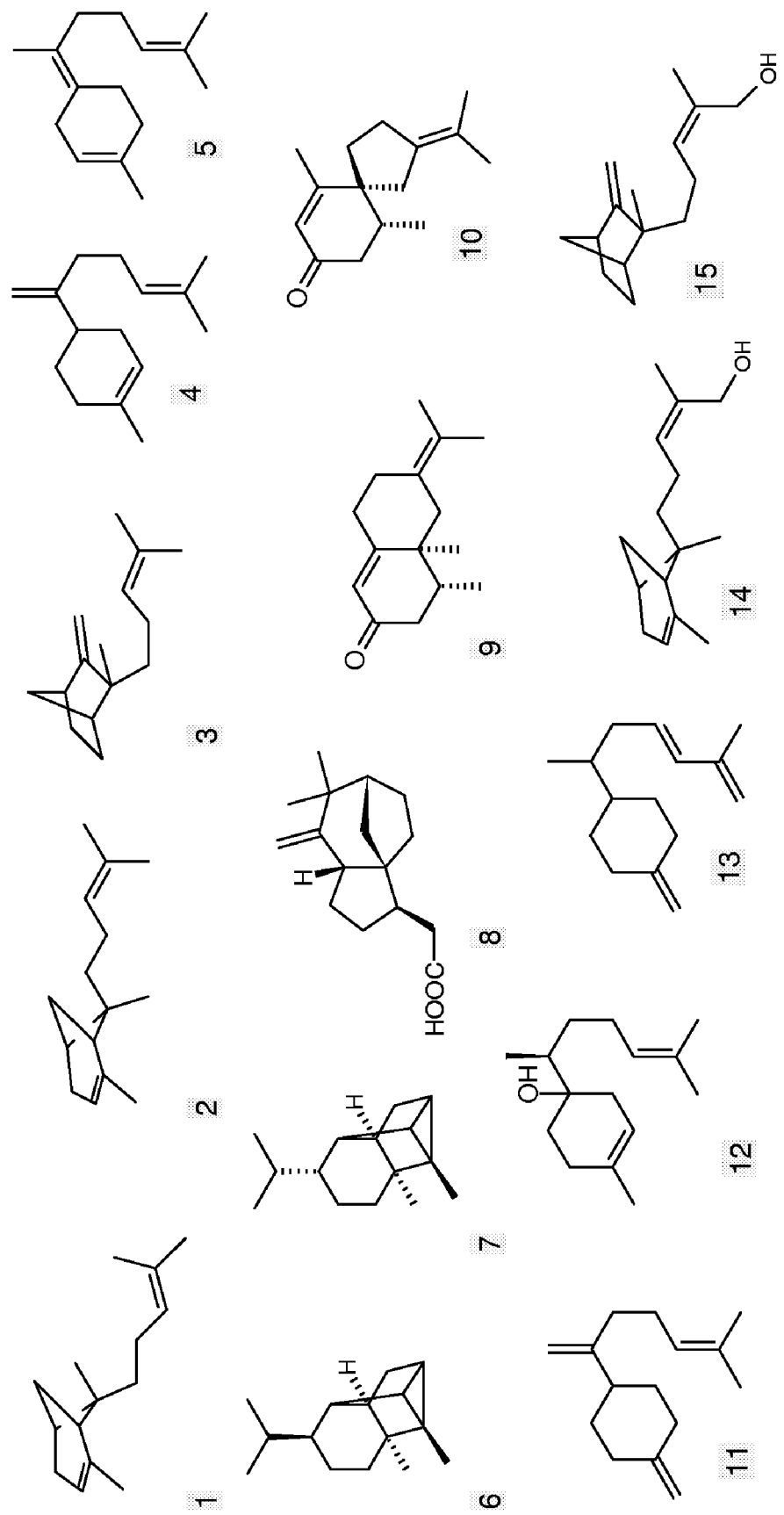
Figure 5:
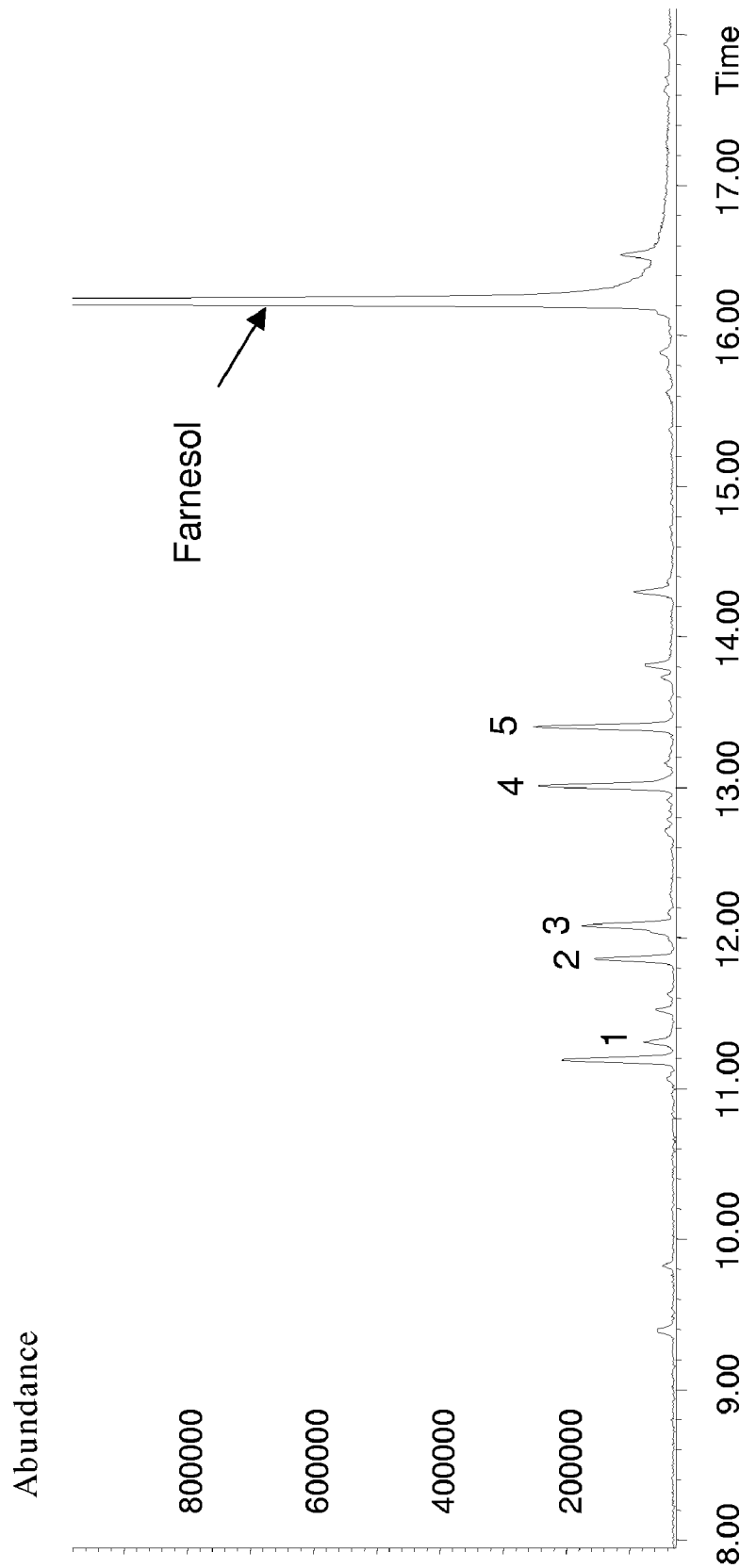

FIG. 5 shows a GC of sesquiterpenes obtained from an enzymatic assay in which FFP was exposed to a polypeptide having an amino acid sequence substantially as set out in SEQ ID NO: 5. This recombinant protein produced a mixture of at least seven different sesquiterpene hydrocarbons, from which 5, indicated as numbers 1-5, have been identified by GC-MS (see FIG. 1 for the name of the compounds).

Figure 6:
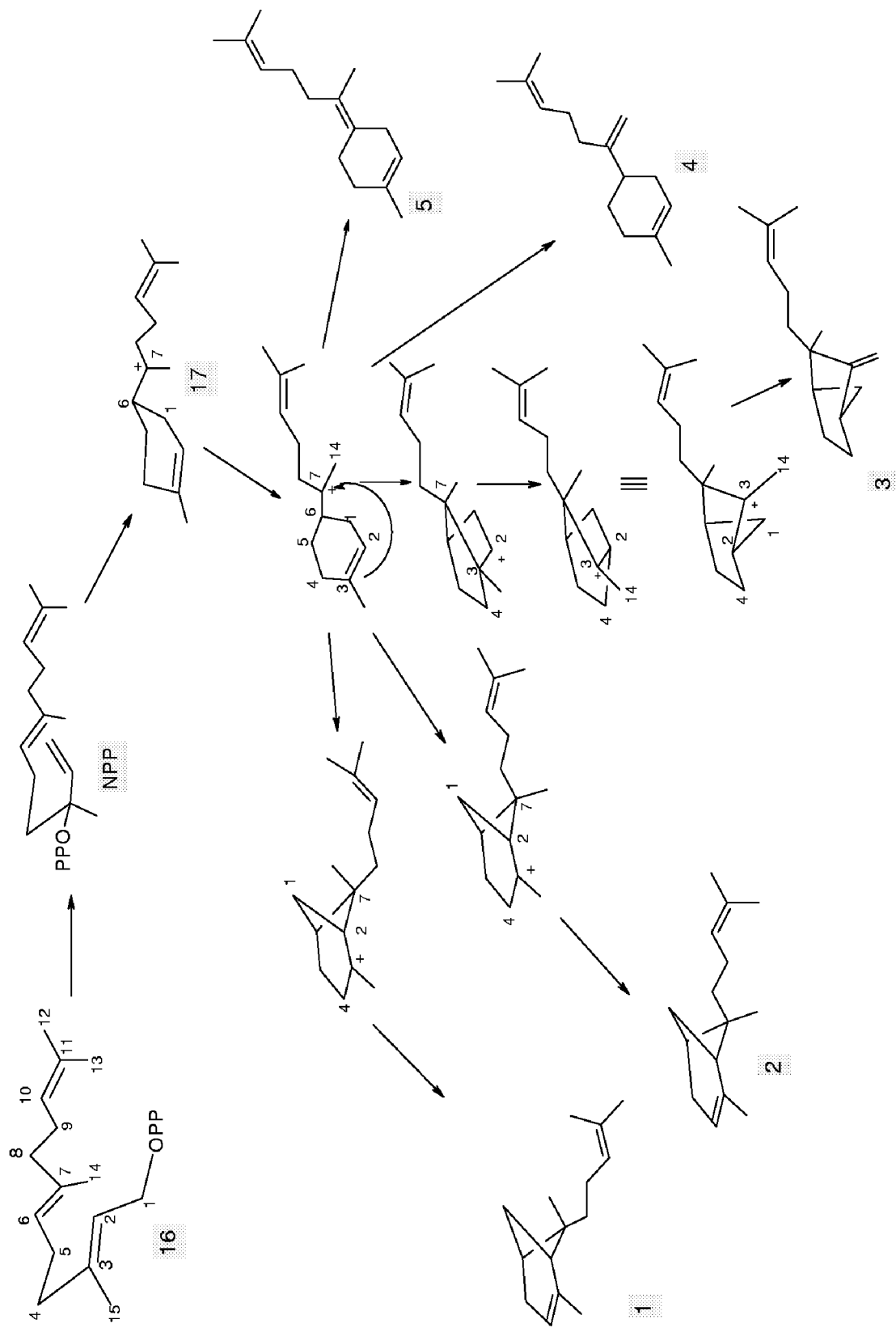

FIG. 6 shows the putative biosynthetic mechanism of the synthesis of sesquiterpenes catalysed by the polypeptides of the present invention, which reaction starts from FPP (16) and passes by the intermediate bisabolyl-cation (17). In particular, the reaction catalysed from polypeptides having an amino acid sequence substantially as set out in SEQ ID NO: 5 and variants thereof. FIG. 6 further shows the chemical structures of the precursor (FPP) and the sesquiterpene products.

| Abbreviations Used | |
|---|---|
| bp | base paire |
| DNA | deoxyribonucleic acid |
| cDNA | complementary DNA |
| DTT | dithiothreitol |

-continued

| Abbreviations Used | |
|---|---|
| FPP | Farnesyl-pyrophosphate |
| NPP | Nerolidol-pyrophosphate |
| IPTG | isopropyl-D-thiogalacto-pyranoside |
| PCR | polymerase chain reaction |
| RT-PCR | reverse transcription - polymerase chain reaction |
| 3'-/5'-RACE | 3' and 5' rapid amplification of cDNA ends |
| RNA | ribonucleic acid |
| mRNA | messenger ribonucleic acid |
| nt | nucleotide |
| RNase | ribonuclease |
| SDS-PAGE | SDS-polyacrylamid gel electrophoresis |

DETAILED DESCRIPTION OF THE PREFERRED EMBODIMENTS

The present invention provides isolated nucleic acids encoding novel sesquiterpene synthases capable of synthesising mono-, bi- and/or tricyclic sesquiterpenes. Bicyclic or tricyclic sesquiterpenes comprising a $C_3$-$C_7$ bond are defined as sesquiterpenes having a santalene carbon skeleton, while those comprising a $C_2$-$C_7$ bond are defined as sesquiterpenes of the bergamotene skeleton.

A "terpene" is an hydrocarbon based on an isoprene unit ($C_5H_8$), which may be acyclic or cyclic. "Terpenes" include but are not limited to cyclosativene, cyclocopacamphene, cyclocopacamphenol epimers, cyclocopacamphenal epimers, cyclocopacamphenic acid epimers, cis-α-bergamotene, trans-α-bergamotene, (+)-epi-β-santalene, β-bisabolene, and trans-γ-bisabolene.

"Terpenes" and "Terpenoids", as used herein include terpenes and terpene derivatives, including compounds that have undergone one or more steps of functionalisation such as hydroxylations, isomerizations, oxido-reductions, dimethylation or acylation. As used herein, a "sesquiterpene" is a terpene based on a $C_{15}$ structure and includes sesquiterpenes and sesquiterpene derivatives, including compounds that have undergone one or more steps of functionalization.

As used herein, a "derivative" is any compound obtained from a known or hypothetical compound and containing essential elements of the parent substance.

As used herein, a "terpene synthase" is any enzyme that catalyses the synthesis of a terpene. A "sesquiterpene synthase" is an enzyme that catalyses the synthesis of a sesquiterpene.

Sequence identity, as used in the term "identity" or "identical" can be readily calculated by standard alignment algorithms. Preferably, for assessing sequence identity of the sequences of the present invention with another sequence, for example from the prior art, CLUSTAL W. is used, as disclosed in J. D. Thompson, D. J. Higgins, T. J. Gibson (1994) CLUSTAL W: improving the sensitivity of progressive multiple sequence alignment through sequence weighting, position-specific gap penalties and weight matrix choice. Nucleic Acids Res 22(22), 4673-4680. The standard parameters are selected for assessing sequence identity. The sequence comparison may be performed on-line, at "www.ebi.ac.uk/clustalw/", or, alternatively, suitable software can be downloaded. For example, the BioEdit software available from www.mbio.ncsu.edu/BioEdit/bioedit.html/.

In an aspect, the present invention provides isolated nucleic acids hybridising to any of the nucleic acids of the invention, such as those detailed under SEQ ID NO: 1, 2 or 3 under low stringency conditions. Preferably, the defined conditions are moderate stringency conditions, more preferably they are high stringency conditions.

Surprisingly, the sequence at the N-term end of SEQ ID NO 6 differs from other known terpene synthase sequences in that it contains an unusual motif PAAAASSQQQQ (SEQ ID NO 7) that does not resemble to any known signal sequence. The present invention is also directed to this particular sequence, and to any nucleotide sequence encoding this motif, such as the one of SEQ ID NO 3.

In a particular embodiment, the invention relates to certain isolated nucleotide sequences including those that are substantially free from contaminating endogenous material. The terms "nucleic acid" or "nucleic acid molecule" include deoxyribonucleotide or ribonucleotide polymers in either single- or double-stranded form (DNA and/or RNA). A "nucleotide sequence" also refers to a polynucleotide molecule or oligonucleotide molecule in the form of a separate fragment or as a component of a larger nucleic acid.

In an embodiment, the present invention provides a nucleic acid selected from: (a) any nucleic acid selected from the group consisting of SEQ ID NO: 1, 2 and 3, (b) any nucleic acid selected from the group consisting of the nucleic acids encoding any of the polypeptides substantially as set out in SEQ ID NO: 4, 5, and 6, (c) a nucleic acid that hybridises to the nucleic acid of (a) or (b) under low stringency conditions, wherein the polypeptide encoded by said nucleic acid has sesquiterpene synthase activity.

In an embodiment, the nucleic acid comprises a nucleotide sequence, which is at least 59%, preferably at least 60%, more preferably at least 65% and most preferably at least 70% identical to SEQ ID NO: 1. For example, the nucleic acid sequence of the invention is at least 75%, 80%, 85%, 90%, 95% or 98% identical to SEQ ID NO: 1.

In an embodiment, the nucleic acid comprises a nucleotide sequence, which is at least 82.4%, preferably at least 85%, more preferably at least 90%, and most preferably at least 95% identical to SEQ ID NO: 2. For example, the nucleic acid sequence of the invention is at least 95%, 97%, or 98% identical to SEQ ID NO: 2.

In an embodiment, the nucleic acid comprises a nucleotide sequence, which is at least 49%, preferably at least 50%, more preferably at least 55% and most preferably at least 60% identical to SEQ ID NO: 3. For example, the nucleic acid sequence of the invention is at least 65%, 70%, 75%, 80%, 85%, 90%, 95% or 98% identical to SEQ ID NO: 3.

Preferably, the nucleic acid of step (c) hybridises under moderate, more preferably under high stringency conditions to the nucleic acids of (a) or (b) above, but preferably to the sequence SEQ ID NO 1, 2, or 3. For example, the nucleic acid of (c) hybridised to SEQ ID NO 1. According to another example, it hybridised to SEQ ID NO 3 under the above-mentioned conditions.

Preferably, the nucleic acids of the invention hybridise with the nucleic acid of SEQ ID NO: 1 and do not hybridise with a nucleic acid encoding a putative sesquiterpene synthase found in *Oryza sativa* under accession number AP003911.

According to an embodiment, the nucleic acids of the invention hybridises with the nucleic acid of SEQ ID NO: 2 and do not hybridise with nucleic acids selected from those having accession numbers AY518310 or AY518313 encoding sesquiterpene synthases in *Zea mays*. Preferably, the nucleic acid of the present invention does further not hybridise with any of the nucleic acid sequences selected from those having accession numbers AY518311, AY518312, and AY518314. These latter sequence are not reported to encode an active sesquiterpene synthase.

Preferably, the nucleic acids of the invention hybridise with the nucleic acid of SEQ ID NO: 3 and do not hybridise with a nucleic acid encoding a putative sesquiterpene synthase found in *Zea mays*, having accession number AAG37841.

Preferably, the isolated nucleic acid, which specifically hybridise with the nucleic acid of SEQ ID NO: 3 under stringent conditions do not hybridise at the stringent conditions with a nucleic acids present in *Zea mays*, putatively encoding terpene synthases having accession number AF296122.

Preferably, the nucleic acid sequence according to the invention comprises SEQ ID NO 1, 2 and/or 3. More preferably, it essentially consists of SEQ ID NO 1, 2 and/or 3.

In another embodiment, the nucleic acid comprises a contiguous fragment of at least 20, 100, 200, 300, 400, 500, or 750 nucleotides of SEQ ID NO 1, 2 and/or 3.

Preferably, the nucleic acid of the invention hybridises to the fragments having the above length under low, moderate or high stringency conditions.

Preferably, the nucleic acid of the invention comprises the fragment from about nt 900 to nt 1647, 1641 and 1791 of SEQ ID NO:1, 2, and/or 3, respectively. These fragments include the active sites of the polypeptides of the invention.

Preferably, a nucleic acid and/or polypeptide of the invention is isolated from Vetiver (*Vetiveria zizanoides*). In an embodiment, the nucleic acid is isolated from Vetiver roots.

As used herein, the term "hybridization or hybridizes under certain conditions" are defined as disclosed below. The conditions may be such that sequences, which are at least about 70%, such as at least about 80%, and such as at least about 85-90% identical, remain bound to each other.

Appropriate hybridization conditions can be selected by those skilled in the art with minimal experimentation as exemplified in Ausubel et al. (1995), Current Protocols in Molecular Biology, John Wiley & Sons, sections 2, 4, and 6. Additionally, stringency conditions are described in Sambrook et al. (1989), chapters 7, 9, and 11.

As used herein, defined conditions of "low stringency" are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used.

Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of "moderate" stringency are different from those of "low" stringency conditions in that filters containing DNA are pretreated for 7 h at 50° C. (moderate) and 8 hours at 65° C. (high) in the corresponding solution given above. Hybridizations are carried out in the same solution as for "low stringency" but for 30 h at 50° C., respectively and then washed for 1.5 h at 55° C. (moderate) in the washing solution detailed above. The wash solution is replaced with fresh solution and incubated an additional 1.5 h at 60° C.

Conditions for "high" stringency: prehybridization for 8 h at 65° C. in solution as above, but with 6×SSC, a nM EDTA, 0.02% PVP, 0.02% Ficoll, 0.02% BSA and 500 µg/ml denatures salmon sperm DNA instead. Filters are hybridized for 48 h at 65° C. in the prehybridization mixture containing 100 µg/ml denatured salmon sperm DNA and 5-20×106 cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min. Other conditions of low, moderate, and high stringency well known in the art (e.g., as employed for cross-species hybridizations) may be used if the above conditions are inappropriate.

The present invention also encompasses "variant nucleotide sequences", obtained by mutations in of any of SEQ ID NO 1, 2, and 3, for example. Mutations may be any kind of mutations of the sequences of the present invention, such as point mutations, deletion mutations, insertion mutations and/or frame shift mutations. Variant nucleotide sequences may be prepared in order to adapt a sequence to a specific expression system. For example, bacterial expression systems are known to more efficiently express polypeptides if amino acids are encoded with a preferred codon. Due to the degeneracy of the genetic code, wherein more than one codon can encode the same amino acid, multiple DNA sequences can code for the same polypeptide, which are encompassed by the nucleic acids or nucleotide sequences of the present invention.

In addition, the present invention also encompasses variant nucleotide sequences encoding polypeptides which are substantially different from the amino acid sequences reported herein, but which are obtained by modifying, e.g. by mutagenesis, or otherwise taking use of the present nucleotide sequences.

Preferably, the polypeptide of the invention is capable of synthesising mono- and bi-cyclic sesquiterpenes. Preferably, it is capable of synthesising bi- or tricyclic sesquiterpenes. Most preferably, it is capable of synthesising mono-, bi-, and tricyclic sesquiterpenes.

Preferably, the isolated polypeptide of the present invention is capable of forming a bisabolyl cation from FPP and capable of further creating a bond between the $C_3$ and the $C_7$ carbon atom of FPP to produce a bi-cyclic or tricyclic sesquiterpene comprising a $C_3$-$C_7$ bond.

Similarly, the polypeptide of the present invention is capable of forming a bisabolyl cation from FPP and capable of further creating a bond between the $C_2$ and the $C_7$ carbon atom of FPP to produce a bi-cyclic or tricyclic sesquiterpene comprising a $C_2$-$C_7$ bond.

The term "capable of synthesising" a compound, such as a specific sesquiterpene, and the terms "terpene synthase activity", preferably "sesquiterpene synthase activity", refers to polypeptides of the present invention, as well as nucleic acids encoding these polypeptides, which are capable of synthesizing a terpene, preferably a sesquiterpene and most preferably the sesquiterpene compounds mentioned herein from at least one starting compound, which preferably is an acyclic pyrophosphate terpene precursor. Preferably, the capacity of synthesising is determined with the enzyme assay detailed in Example 5. If a specific product is detected by this assay, the "capacity of synthesising", or "synthase activity" it is given for the product. Preferably, the acyclic terpene precursor is FPP, which is given in formula (I) below with standard numeration of the carbon skeleton of sesquiterpenes. OPP refers to pyrophosphate.

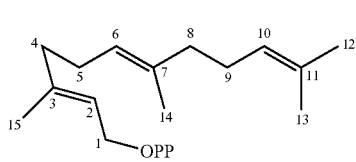

(I)

(IV)

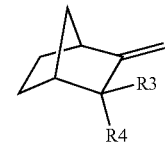

(V)

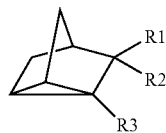

(VI)

Preferably, the isolated polypeptide is capable of synthesising at least one sesquiterpene, more preferably at least one sesquiterpene having a santalene or bergamotene carbon skeleton. In a preferred embodiment, the polypeptide is capable of forming a bisabolyl cation from FPP, and capable of further creating a bond between the $C_3$ or $C_2$ and the $C_7$ carbon atom of FPP to produce one or several bi-cyclic and/or tricyclic sesquiterpenes.

The term "bond" refers to a single covalent bond.

The present invention relates to nucleic acids encoding a polypeptide, as well as to the polypeptide itself, capable of synthesising at least one bi-cyclic and/or tri-cyclic sesquiterpene comprising a $C_3$-$C_7$ bond. Preferably, the sesquiterpenes comprising a $C_3$-$C_7$ bond constitute at least 5 wt. % of the sesquiterpene products synthesised by the polypeptide. More preferably, at least 10 wt %, even more preferably at least 15 wt %, and most preferably at least 20 wt % of the sesquiterpenes produced by the polypeptide are constituted by sesquiterpenes having a $C_3$-$C_7$ bond. The quantitative sesquiterpene product distribution of a sesquiterpene synthase, for the purpose of the present invention, is preferably determined by employing the procedure detailed in Example 5 (enzyme assay, extraction of products and GC).

Accordingly, the present invention relates to isolated polypeptides capable of forming compounds having a $C_3$-$C_7$ bond of the formula (II) and/or (III) below

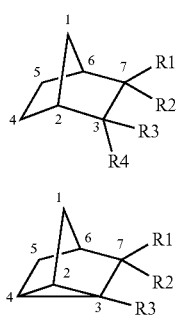

in which $R_1$, $R_2$, $R_3$, $R_4$ are, independently of each other, a linear or branched alkyl or alkylene group from $C_1$ to $C_{20}$, and whereby $R_1$ and $R_2$ and/or $R_3$ and $R_4$ may form a double bond instead of two individual single bonds.

Preferably, $R_1$, $R_2$, $R_3$, $R_4$ are, independently of each other, a linear or branched alkyl or alkylene group from $C_1$ to $C_{15}$, more preferably from $C_1$ to $C_{10}$, most preferably, from $C_1$ to $C_8$.

In particular, the polypeptides of the present invention are capable of forming compounds of the formula (IV), (V) and/or (VI) below in which $R_1$, $R_2$, $R_3$, $R_4$ are defined as above.

Preferably, in formula (IV) and/or (VI), either $R_1$ or $R_2$ is a $C_1$-$C_5$ alkyl and the other is a $C_2$-$C_8$ alkylene. In addition $R_3$ in formula (VI) preferably is a $C_1$-$C_5$, more preferably a $C_1$-$C_3$ alkyl. Preferably, in formula (V), $R_3$ and $R_4$ are defined as $R_1$ and $R_2$ in formula (IV) above.

The present invention relates to nucleic acids encoding a polypeptide, and to the polypeptide it-selves, capable of forming at least one sesquiterpene having a $C_2$-$C_7$ bond.

According to a preferred embodiment, sesquiterpenes comprising a $C_2$-$C_7$ bond constitutes at least 5 wt. % of the sesquiterpene products synthesised by the polypeptide. More preferably, at least 10 wt %, even more preferably at least 15 wt %, and most preferably at least 20 wt % of the sesquiterpenes produced by the polypeptide are constituted by the sesquiterpene having a $C_2$-$C_7$ bond. Preferably, the sesquiterpene is bergamotene and/or one of its isomers, preferably stereoisomers.

According to an embodiment, the present invention relates to isolated polypeptides capable of forming compounds having a $C_2$-$C_7$ bond according to the formula (VII) and/or (VIII) below

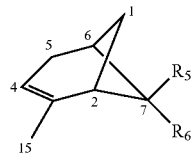

(VII)

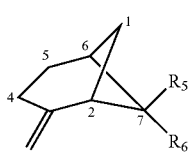

(VIII)

in which $R_5$ and $R_6$ are defined as $R_1$ and $R_2$ above. Preferably, $R_5$ is a methyl and $R_6$ is a $C_2$-$C_{10}$ alkenyl, or vice versa.

Preferably, at least one alkenyl possibly present in one of the residues $R_1$, $R_2$, $R_3$, $R_4$, $R_5$ or $R_6$ mentioned above is 4-methyl-3-pentenyl, while another residue linked to the same carbon atom is methyl.

The polypeptides capable of synthesizing the compounds of formulae (II), (III), (IV), (V), (VI), (VII) and/or (VIII) above preferably are the polypeptides having the amino acid sequence SEQ ID NO: 5, or polypeptide variants thereof.

Sesquiterpenes having a $C_3$-$C_7$ bond are santalene and its stereoisomers, in particular (+)-epi-β-santalene, (−)-β-santalene, (+)-β-santalene (all three of which are bi-cyclic), and (+)-α-santalene, and (−)-α-santalene (both of which are tri-cyclic), for example.

Sesquiterpenes having a $C_2$-$C_7$ bond are bergamotene including its stereoisomers, in particular, cis-α-bergamotene, trans-α-bergamotene, trans-β-bergamotene and cis-β-bergamotene, for example.

Most preferably, the polypeptides of the present invention are capable of synthesizing the compounds reproduced in the figures.

In a further aspect, the invention provides an isolated polypeptide capable of synthesising santalene, bergamotene, and/or bisabolene.

In a preferred embodiment, the invention provides an isolated polypeptide capable of synthesising (+)-epi-β-santalene, trans-α-bergamotene, cis-α-bergamotene, β-bisabolene, and/or trans-γ-bisabolene.

Preferably, the polypeptide is capable of synthesizing any or all of (+)-epi-β-santalene, trans-α-bergamotene, cis-α-bergamotene, β-bisabolene, and/or trans-γ-bisabolene. More preferably, the polypeptide is capable of synthesizing at least one of them. Most preferably, the polypeptide is capable of synthetizing (+)-epi-β-santalene, trans-α-bergamotene and/or cis-α-bergamotene.

As used herein, the term "polypeptides" refers to a genus of polypeptide or peptide fragments that encompass the amino acid sequences identified herein, as well as smaller fragments.

A "polypeptide variant" as referred to herein means a polypeptide substantially homologous to a native polypeptide, but which has an amino acid sequence different from that encoded by any of the nucleic acid sequences of the invention because of one or more deletions, insertions or substitutions.

The polypeptide, and polypeptide variants of the present invention preferably have terpene synthase activity. More preferably, they have sesquiterpene synthase activity.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, Biochemistry, Addison-Wesley Pub. Co., (1983). The effects of such substitutions can be calculated using substitution score matrices such a PAM-120, PAM-200, and PAM-250 as discussed in Altschul, (J. Mol. Biol. 219:555-65, 1991). Other such conservative substitutions, for example, substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the sesquiterpenes synthases of the invention may be used to attain desired enhanced or reduced enzymatic activity, modified regiochemistry or stereochemistry, or altered substrate utilization or product distribution. Furthermore, variants may be prepared to have at least one modified property, for example an increased affinity for the substrate, an improved specificity for the production of one or more desired compounds, a different product distribution, a different enzymatic activity, an increase of the velocity of the enzyme reaction, a higher activity or stability in a specific environment (pH, temperature, solvent, etc), or an improved expression level in a desired expression system. A variant or site direct mutant may be made by any method known in the art. As stated above, the invention provides recombinant and non-recombinant, isolated and purified polypeptides, such as from Vetiver plants. Variants and derivatives of native polypeptides can be obtained by isolating naturally-occurring variants, or the nucleotide sequence of variants, of other or same plant lines or species, or by artificially programming mutations of nucleotide sequences coding for native terpene synthases. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, aid in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or polypeptides which are linked to signal peptides.

Therefore, in an embodiment, the present invention provides a method for preparing a variant polypeptide having a desired terpene synthase activity, the method comprising the steps of:

(a) selecting any of the nucleic acids from the group consisting of SEQ ID NO 1, 2 or 3, or nucleic acids therewith related therewith comprising nucleotide sequences described above;
(b) modifying the selected nucleic acid to obtain at least one mutant nucleic acid;
(c) transforming host cells with the mutant nucleic acid sequence to express a polypeptide encoded by the mutant nucleic acid sequence;
(d) screening the polypeptide for a functional polypeptide having at least one modified property; and,
(e) optionally, if the polypeptide has no desired variant terpene synthase activity, repeat the process steps (a) to (d) until a polypeptide with a desired variant terpene synthase activity is obtained (=DNA shuffling).

The method for providing a variant polypeptide is suitable of screening and functional polypeptides having a desirable property, such as activity parameter, from polypeptides encoded by a pool of mutant nucleic acids. In step (a), any of the nucleic acids of the present invention may be selected.

Thereafter, in step (b), a large number of mutant nucleic acid sequences may be created, for example by random mutagenesis, site-specific mutagenesis, or DNA shuffling. The detailed procedures of gene shuffling are found in Stemmer, W. P. (1994) DNA shuffling by random fragmentation and reassembly: in vitro recombination for molecular evolution. Proc Natl Acad Sci USA. 91(22): 10747-1075. In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Accordingly, any of SEQ ID NO 1, 2 or 3 may be recombined with a different sequence selected from any of SEQ ID NO 1, 2 or 3, and/or with other terpene synthase encoding nucleic acids, for example isolated from an organism other than *Vetiver zizanoides*. Thus, mutant nucleic acids may be obtained and separated, which may be used for transforming a host cells according to standard procedures, for example such as disclosed in the present examples.

In step (d), the polypeptide obtained in step (e) is screened for a modified property, for example a desired modified enzymatic activity. Examples, for desired enzymatic activities for which an expressed polypeptide may be screened include enhanced or reduced enzymatic activity, as measured by $K_M$ or $V_{max}$ value, for example, modified regio-chemistry or stereochemistry, altered substrate utilization or product distribution. The screening of enzymatic activity can be performed according to procedures familiar to the skilled person and those disclosed in the present examples.

Step (e) provides for repetition of process steps (a)-(d), which may, preferably, performed in parallel. Accordingly, by creating a significant number of mutant nucleic acids, many host cells may be transformed with different mutant nucleic acids at the same time, allowing for the subsequent screening of a elevated number of polypeptides. The chances of obtaining a desired variant polypeptide may thus be increased at the discretion of the skilled person.

In an embodiment, the present invention provides a method for preparing a nucleic acid encoding a variant polypeptide having terpene synthase activity, the method comprising the steps (a)-(e) disclosed above and further comprising the step of:

(f) if a polypeptide having desired variant terpene activity was identified, acquiring the mutant nucleic acid obtained in step (c), which was used to transform host cells to express the variant terpene synthase following steps (c) and (d).

Polypeptide variants also include polypeptides having a specific minimal sequence identity with any of the polypeptides comprising the amino acid sequences according to SEQ ID NO: 4, 5, and/or 6.

In an embodiment, the isolated polypeptide comprising an amino acid sequence which has at least 50% of amino acid sequence identity with SEQ ID NO: 4 and which has terpene synthase activity. Preferably, the isolated polypeptide comprises an amino acid sequence, which has at least 55%, 60%, 65%, 70%, 75%, 80%, 90%, and most preferably 95% of sequence identity with SEQ ID NO: 4.

In an embodiment, the isolated polypeptide comprising an amino acid sequence which has at least 76.8% of amino acid sequence identity with SEQ ID NO: 5 and which has terpene synthase activity. Preferably, the isolated polypeptide comprises an amino acid sequence, which has at least 78%, 79%, 80%, 85%, 90%, 95% and most preferably 97% of sequence identity with SEQ ID NO: 5.

In an embodiment, the isolated polypeptide comprising an amino acid sequence which has at least 49% of amino acid sequence identity with SEQ ID NO: 6 and which has terpene synthase activity. Preferably, the isolated polypeptide comprises an amino acid sequence, which has at least 50%, 55%, 60%, 65%, 70%, 75%, 80%, 85%, 90%, 95% and more preferably 97% of sequence identity with SEQ ID NO: 6.

Preferably, the polypeptide essentially consists of an amino acid sequence according to SEQ ID NO: 4, 5 or 6.

In a further aspect, the invention provides a vector comprising the nucleic acid of the invention.

A "vector" as used herein includes any recombinant vector including but not limited to viral vectors, bacteriophages and plasmids. The skilled person is capable of selecting a suitable vector according to the expression system. In one embodiment, the expression vectors include a cDNA sequence encoding the polypeptide operably linked to regulatory sequences such as transcriptional promoters, operators, or enhancers, mRNA ribosomal binding sites, and appropriate sequences which control transcription and translation initiation and termination for example. Nucleotide sequences are "operably linked" when the regulatory sequence functionally relates to the cDNA sequence of the invention.

The vectors of the present invention may be used in the methods for preparing a genetically modified host organisms and/or cells, in host organisms and/or cells harbouring the nucleic acids of the invention and in the methods for producing or making terpene synthases, as is set out further below.

In an aspect, the present invention provides a method of making a terpene synthase comprising, culturing a host organism and/or cell modified to contain at least one nucleic acid sequence under conditions conducive to the production of said terpene synthase, wherein said at least one nucleic acid is the nucleic acid according to the invention.

For example, the method of producing a terpene synthase comprises the steps of
(a) selecting a host organism and/or cell which does not express the nucleic acids according to the invention;
(b) transforming the organism to express the nucleic acid according to the invention;
(c) culturing the organism under conditions conducive to the production of the terpene synthase encoded by said nucleic acid.

The present invention also provides a method of producing a terpene synthase, the method comprising the steps of
(a) selecting a host organism and/or cell which does express any of the nucleic acids according to the invention;
(b) transforming the organism to express the nucleic acid according to any of claims 1-3 or 12 in higher quantity;
(c) culturing the organism under conditions conducive to the production of the terpene synthase encoded by said nucleic acid.

Accordingly, in a further aspect, the present invention provides a recombinant host organism and/or cell transformed to harbour the nucleic acid of the invention. The host organism may be a unicellular or a multi-cellular organism, but is non-human. The host may be a cell of a multicellular organism, for example. Preferably, the host organism is a bacterium, for example *E. coli*. Preferably, the host organism heterologously comprises a nucleic acid of the invention.

Further preferred host organisms include fungi, preferably yeasts, most preferably *Sacharomyces cerevisiae*. Suitable host organisms for expression of polypeptides of the invention include higher eukaryotic cells, preferably plants. Preferably, the plant is a species belonging to the family of the Solanaceae or Lamiaceae, more preferably the genus of *Nicotiana*. For example, the suitable host cell is a plant cell.

In an aspect, the present invention provides a recombinant host organism or cell expressing the polypeptide of the present invention. Preferably, the host organism is transformed to express the polypeptide in a higher quantity than in the same organism not so transformed.

The term "transformed" refers to the fact that the host was subjected to genetic engineering to comprise one, two or more copies of any of the nucleic acids of the invention.

Preferably, the term "transformed" relates to hosts heterologuously expressing polypeptides of the invention and/or encoded by nucleic acids of the invention.

Accordingly, in an embodiment, the present invention provides a transformed organism in which the polypeptide of the invention is expressed in a higher quantity than in the same organism not so transformed.

There are several methods known in the art for the creation of transgenic, recombinant host organisms or cells such as plants, yeasts, bacteria, or cell cultures of higher eukaryotic organisms. For example, appropriate cloning and expression vectors for use with bacterial, fungal, yeast, and mammalian cellular hosts are described, for example, in Pouwels et al., Cloning Vectors: A Laboratory Manual, Elsevier, N.Y., (1985), and Sambrook et al. cited above.

Cloning and expression vectors for higher plants and/or plant cells in particular are available to the skilled person, see for example Schardl et al (1987) Gene 61: 1-11.

Methods for transforming host-organisms, for example, producing transgenic plants, modifying host organisms or cells to harbour transgenic nucleic acids, such as those of the present invention, are familiar to the skilled person. For the creation of transgenic plants, for example, current methods include: electroporation of plant protoplasts, liposome-mediated transformation, *agrobacterium*-mediated transformation, polyethylene-glycol-mediated transformation, particle bombardement, microinjection of plant cells, and transformation using viruses.

In one embodiment, transformed DNA is integrated into a chromosome of a non-human host organism and/or cell such that a stable recombinant systems results. Any chromosomal integration method known in the art may be used in the practice of the invention, including but not limited to, recombinase-mediated cassette exchange (RMCE), viral site-specific chromosomal insertion, adenovirus, and pronuclear injection.

In a still further aspect, the present invention provides processes and/or methods for making terpenoids.

Accordingly, the present invention provides a method of making at least one terpenoid comprising:

(a) contacting at least one acyclic pyrophosphate terpene precursor with at least one polypeptide of the invention or encoded by any of the nucleic acids of the invention, and, (b) optionally, isolating at least one terpenoid produced in step (a).

Furthermore, the present invention provides a method of making at least one terpenoid comprising:

cultivating a non-human organism transformed to express or increasingly express the polypeptide encoded by the nucleic acid of any of claims 1-3 or the polypeptide of claim 4 under conditions conducive to the production of terpenoids, and, optionally, isolating at least one terpenoid from the non-human organism.

According to a preferred embodiment, the method further comprises the step of: transforming a non-human organism with a recombinant nucleic acid to express or increasingly express the polypeptide encoded by the nucleic acid of any of claims 1-3 or the polypeptide of claim 4, before the step of cultivating said organism under conditions conducive to the production of terpenoids.

Preferably, the at least one terpenoid is the terpenoid disclosed in the present description. More preferably, the methods are suitable to make at least one cyclic terpene according to formulae (I) to (VII).

The method of making at least one terpenoid comprises the step of contacting at least one acyclic pyrophosphate terpene precursor with at least one polypeptide of the invention. For example, polypeptides as obtained in the above methods for producing terpene synthases may be used. Such polypeptides may be extracted from host organisms expressing the nucleic acids of the invention according to standard protein or enzyme extraction technologies. If the host organism is a unicellular organism or cell releasing the polypeptide of the invention into the culture medium, the polypeptide may simply be collected from the culture medium, for example by centrifugation, optionally followed by washing steps and resuspension in suitable buffer solutions.

If the host organism is a plant or a unicellular organism or cell accumulating the polypeptide of the invention within the cell, the polypeptide may be obtained by disruption or lysis of the cells and extracting the polypeptide from the cell lysate.

The isolated polypeptide may then suspended in a buffer solution at optimal pH and temperature. If adequate, salts, BSA and other kinds of enzymatic co-factors may be added in order to optimise enzyme activity.

The terpene precursor may be added to polypeptide suspension or solution, followed by incubation at optimal temperature, for example 30° C. After incubation, the terpenoid compound may be isolated from the incubated solution by standard isolation procedures, such as solvent extraction and distillation, preferably after removal of polypeptides from the solution.

In a step of the process for making at least one terpenoid compound, the host organism or cell is cultivated under conditions conducive to the production of terpenoids. Accordingly, if the host is a transgenic plant, optimal growing conditions are provided, such as optimal light, water and nutient conditions, for example. If the host is a unicellular organism, conditions conducive to the production of the terpenoid may comprise addition of suitable cofactors to the culture medium of the host. In addition, a culture medium may be selected which proves to maximize terpenoid synthesis. External factors such as optimised pH and temperature are usually also conducive to terpenoid production in a given expression system.

All the publications mentioned in this application are incorporated by reference to disclose and describe the methods and/or materials in connection with which the publications are cited.

The following examples are intended to illustrate the invention without limiting the scope as a result.

EXAMPLES

Example 1

Vetiver Roots Material, Isolation of mRNA and cDNA Synthesis

*Vetiveria zizanoides* (Vetiver) plants were obtained from a plant nurseries ('La Compagnie des Plantes Australes', Les Avirons, The Réunion Island, France). The plants were cultivated in pots in a green house at the Lullier Agronomy research Station (Switzerland) and were propagated vegetatively by dividing six months to one-year-old clumps. In the greenhouse conditions, transplanted vetiver cuttings start sprouting after one to three weeks and the roots volume is generally tripled or quadrupled after one-year cultivation.

For harvesting of the roots, the plants were dug out from the pots and rinsed with tap water. The sesquiterpene content of the roots was evaluated as follows: the roots were cut in small pieces or crushed in liquid nitrogen using a mortar and pestle and extracted with diethyl ether or pentane; after concentration, the extracts were analyzed by GC and GC-MS. Plants obtained after transplantation of splits from a mother plant were harvested at different growing stages: from plants with actively expending root system (4 to 6 months after transplantation) to plants with a well-developed dense root system (1 to 2 years after transplantation). Sesquiterpenes characteristic of vetiver oil were found in all roots analysed and zizanoic acid was the major constituent.

For the cloning experiments, young plants, obtained approximately 6 month after transplantation, were used. The roots were cut off from the leaves and frozen in liquid nitrogen. They were first roughly chopped in liquid nitrogen using a Waring Blendor and then grounded to a fine powder using a mortar and pestle. Total RNA were extracted using the Concert™ Plant RNA Reagent from Invitrogen following the manufacturer's instructions. The concentration of RNA was estimated from the OD at 260 nm and the integrity of the RNA was evaluated on an agarose gel by verifying the integrity of the ribosomal RNA bands. The mRNA were purified from the total RNA by oligodT-cellulose affinity chromatography using the FastTrack® 2.0 mRNA isolation Kit (Invitrogen) following the manufacturer's instructions. The concentration of the mRNA was estimated from the OD at 260 nm and an aliquot was deposited on an agarose gel to verify the size distribution of the mRNA pool.

Adaptor ligated double stranded cDNA was prepared from the 1 µg of mRNA using the Marathon™ cDNA Amplification Kit (Clontech) following the manufacturer's protocol. An aliquot of the cDNA library was deposited on an agarose gel to evaluate the quantity and size distribution.

Example 2

Isolation of Fragments of cDNA Encoding for Sesquiterpene Synthases from Vetiver Roots Fragments of cDNA encoding for sesquiterpene synthases were amplified using degenerated primers specific for plant sesquiterpene synthases nucleotidic sequences.

Sesquiterpene-synthase-specific oligonucleotides have been previously designed from an alignment of plant sesquiterpene synthases amino-acid sequences (WO 04/031376). Six primers (four forward and two reverse) were designed from three regions conserved among the plant sesquiterpene synthases amino-acid sequences. They were named TpsVF1, TpsVF2, TpsCF1, TpsCF2, TpsVR3 and TpsCR3 (WO 04/031376). In addition, a set of oligonucleotides was designed for improved specificity towards sesquiterpene synthases nucleotidic sequences of vetiver. Sequence comparison of terpene synthases isolated from different plants has shown high sequence homologies in relation to phylogeny. The sequence homology is high among terpene synthases from taxonomically related species and is not related to functional specialization (enzymatic activity). We thus decided to design new sesquiterpene synthases-specific primers based on the alignment of the sequence of sesquiterpene synthases obtained from plant species related to vetiver. Vetiver is a Gramineae plant (grass family) and belongs to the Monocotyledons class (Liliopsida). The amino-acid sequences of sesquiterpene synthases from monocotyledon plants (accession number AAC31570 from *Elaeis oleifera* (oil palm), accession numbers BAC99549, BAC99543, AAR01759, BAD03024, NP_908798, BAC20102, AAR87368 from *Oryza sativa* (Rice) and accession numbers AAG37841, AAS88575, AAS88574, AAS88573, AAS88572, AAS88571 from *Zea mays* (corn)) were aligned using ClustalW [Thompson, J. D., Higgins, D. G. and Gibson, T. J. (1994) CLUSTAL W: improving the sensitivity of progressive multiple sequence alignment through sequence weighting, position specific gap penalties and weight matrix choice. Nucleic Acids Res. 22, 4673-4680] and regions conserved across all sequences were selected. From these regions, primers were design using the CODEHOP strategy [Rose T. M., Schultz E. R., Henikoff J. G, Pietrokovski S. McCallum C. M and Nenikoff S. (1998) Consensus-degenerated hybrid oligo-nucleotide primers for amplification of distantly related sequences. Nucleic Acids Research 26(7), 1628-1635] implemented as a computer program accessible over the World Wide Web "blocks.fhcrc.org/blocks/makeblocks.html" and "blocks.fhcrc.org/blocks/codehop.html". The parameters of the program were set so as to design primers with a degenerated core of 11 to 13 bases, a maximum degeneracy (number of different sequences specified by each primer) of 256 and an annealing temperature around 60° C. The codon usage of the monocotyledon plant *Zea mays* was used. Using this approach, four forward primers and two reverse primers were designed from five conserved regions (Table 1).

TABLE 1

Monocotyledon sesquiterpene-synthases-specific primers

| SEQ ID NO | Primer name | Sequence |
|---|---|---|
| 15 | Tps_monocot_F1 | 5'- CGG TTC TAC CTG CTG CGG mar mab ggn ta -3'<br>     R   F   Y   L   L   R   K   N   G   Y<br>                                    Q   Q<br>                                    H |
| 16 | Tps_monocot_F2 | 5'- CC AGG TCC CTG CTG ACC ytn tay ran gc -3'<br>    T   R   S   L   L   S   L   Y   N   A<br>                                       E<br>                                     D |

TABLE 1-continued

Monocotyledon sesquiterpene-synthases-specific primers

| SEQ ID NO | Primer name | Sequence |
|---|---|---|
| 17 | Tps_monocot_F3 | 5'- GCC GTG CTG GAG CTG GCC aar ytn ray tty -3'<br>A   V   L   E   L   A   K   L   N   F<br>                                        D |
| 18 | Tps_monocot_F4 | 5'- CGG GAC CGG ATC GTG GAG rhn yay tty tgg -3'<br>R   D   R   I   V   E   E   Y   F   W<br>                                M<br>                                A<br>                                C |
| 19 | Tps_monocot_R1 | 3'- ctr ctr wan awr ctG TGG GTG CCG TGG TGG -5'<br>D   D   M   F   D   T   H   G   T   T<br>        I<br>        Y<br>        F |
| 20 | Tps_monocot_R2 | 3'- ctr ctr trn awr ctG TGG GTG CCG TGG TGG -5'<br>D   D   M   F   D   T   H   G   T   T<br>        I<br>        Y<br>        T |

For each primer in table 1 the nucleotide sequence is given and the corresponding amino acid sequence in the alignment is shown. The degeneracies in the nucleotides sequences are indicated using the IUPAC one letter code.

These primers were used in RT-PCR experiments with total RNA extracted from vetiver roots.

In all experiments, the reverse transcriptions were performed at 60° C., using vetiver roots total RNA, an oligo (dT)$_{20}$ primer and the Thermoscrip™ reverse transcriptase (Invitrogen) as described by the manufacturer.

The PCR conditions were adapted for the two sets of primers. With the plant-sesquiterpene-synthases-specific primers, the PCR were performed using the Platinum® Taq DNA polymerase (Invitrogen). The different possible combinations of the forward primers TpsVF1, TpsVF2, TpsCF1 and TpsCF2 and the reverse primers TpsVR3, TpsCR3 and dTadaptor primer (Table 2) were used for the first round PCR. The PCR mix contained 5 µL 10×PCR reaction buffer (invitrogen), 1.5 mM MgCl$_2$, 0.2 mM dNTPs, 200 nM forward primer, 200 nM reverse primer, 0.4 µL (2 units) Platinum® Taq DNA polymerase, 2 µL of cDNA from the reverse transcription described above and distilled water to a final volume of 50 µL. The reactions were performed on a Eppendorf Mastercycler Gradiant thermal cycler and the cycling conditions were as follows: 2 min at 95° C.; 35 cycles of 45 sec at 94° C., 45 sec at 42° C., 2 min 30 sec at 72° C.; and 10 min final extension at 72° C. A second round of PCR was performed with the same conditions as for the first round of PCR using as template 5 µL of the first PCR mixture and the same primers or nested primers. The size of the PCR products were evaluated on a 1% agarose gel. Among the several RT-PCR, two produced the expected fragments: TpsCF1+dTadaptor in the first PCR followed by TpsCF2+TpsCR3 in the second PCR, and TpsCF2+dTadaptor in the first PCR followed by TpsCF2+TpsCR3 in the second PCR. The bands were excised from the gel, purified using the QIAquick® Gel Extraction Kit (Qiagen) and cloned in the pCR®2.1-TOPO vector using the TOPO TA cloning Kit (Invitrogen). Inserted cDNAs were then subject to DNA sequencing and the sequences compared against the GenBank non-redundant protein database (NCBI) using the BLASTX algorithm (Altschul, S. F., Gish, W., Miller, W., Myers, E. W., and Lipman, D. J. (1990) Basic local alignment search tool. *J. Mol. Biol.* 215, 403-410). The comparison was performed on-line at "www.ncbi.nlm.nih.gov/BLAST/". The sequence analysis revealed homology with sesquiterpene synthases and comparison of the sequences showed that we had four distinct fragments of cDNA with significant sequence differences: CA711, CA717, CA782 and CA783 (FIG. 2).

With the monocot-sesquiterpene-synthases-specific primers, The PCR steps were performed using the Advantage 2 Polymerase Mix from Clontech. Each PCR mixture contained 5 µL of Advantage 2 PCR Buffer, 200 µM dNTPs, 200 nM each oligonucleotide primer, 2 µL of cDNA from the reverse transcription described above, 1 µL of Advantage 2 Polymerase Mix and distilled water to a final volume of 50 µL. The following conditions were used for the amplifications: 3 minutes of denaturation at 94° C.; 15 cycles of 1 minutes denaturation at 94° C., 1 min of annealing at 65° C. for the first cycle and minus one degree for each following cycle, and 2 minutes extension at 72° C.; 20 cycles of 1 minutes denaturation at 94° C., 1 min of annealing at 58° C. and 2 minutes extension at 72° C.; and finally 10 minutes extension at 72° C. Different PCR were performed with the possible combination of monocot-sesquiterpene-synthases-specific forward and reverse primers. A second round of PCR was performed using as template 5 µL of the first PCR mixture, with the same conditions and same primers as described above for the first round of PCR. The combination of forward and reverse primers TpsmonocotF3+TpsMonocotR1, TpsmonocotF3+TpsMonocotR2, TpsmonocotF4+TpsMonocotR1 and TpsmonocotF4+TpsMonocotR2 produced amplicons with the expected size. Sequence analysis and comparison showed that we had partial cDNA encoding for three distinct and new sesquiterpene synthases: CA725, CA731 and CA733 (FIG. 2).

Example 3

Amplification of Full-length cDNA Encoding for Sesquiterpene Synthases by Rapid Amplification of cDNA Ends (RACE)

Forward specific primers were designed from these new cDNA fragments (Table 2). 3'RACE was performed as follows. First, a reverse transcription was performed at 60° C. using the oligo(dT)$_{20}$ primer, 1.5 microg of total RNA and the Thermoscrip™ reverse transcriptase, in the same condition as described above for the RT-PCR. A first PCR was performed using the dTadaptor primer and a forward cDNA-specific primer. The PCR mixture contained 0.4 µM cDNA-specific primer, 0.4 µM of dTadaptor primer (Table 2), 300 µM each dNTPs, 5 µL of 10× HotStartTaq® DNA polymerase buffer (Qiagen), 2 µL of the cDNA, 0.5 µL of HotStartTaq® DNA polymerase in a final volume of 50 µL. The cycling conditions were: 15 min at 95° C.; 35 cycles of 45 sec at 94° C., 45 sec at 48° C. and 2 min 30 sec at 72° C.; and 10 min at 72° C. A nested PCR was performed using a PCR mixture with the same composition as above except for the following modifications: a nested cDNA-specific primer and the adaptor P primer (Table 2) were used, 5 mL of the first PCR was used for the template, and the annealing temperature was increased to 60° C. The amplification products were evaluated, subcloned, and their sequence analyzed as described above. The 3'RACE succeeded for CA717 and CA733 (FIG. 3), but not for the other cDNAs. A 3'RACE experiment with the Thermoscrip™ and the primers CA711_F1 and CA711_F2 (Table 2) and with an annealing temperature of the nested PCR lowered at 48° C. instead of 60° C., allowed the non-specific amplification of the 3' end of a new sesquiterpene synthase cDNA, named CA775.

TABLE 2

Primers used for 3'RACE and 5'RACE

| SEQ ID NO | Primer name | Sequence (5' to 3') |
|---|---|---|
| 27 | CA711_F1 | CTCACGAGGACGAATAATATTGAAGAAGGTCC |
| 28 | CA711_F2 | ATTGAAGAAGGTCCTTGGCATTGTTTCC |
| 29 | CA717_F1 | GCTCGGAGTGGTTTACGAGCCCTATTATCC |
| 30 | CA717_F2 | GATGACAAAGTTCATCGTACTTGCATCCTTGC |
|  | CA725_F1 | CTGCGCCGCCTGCATCGCG |
|  | CA725_F2 | GCGCCTGGCGGACTGCAGGGAGG |
|  | CA731_F1 | CCCTGGGAGGAGTGCTCTCGTTCAC |
|  | CA731_F2 | GGATAGTTCTCACCAAAGTTATTGCATTTGCG |
| 35 | CA733_F1 | ATGAACGGGGTATGCTATCACCCTCC |
|  | CA733_F2 | CACCCTCCATACTCTCATTCCCG |
|  | CA775_R | GGTGGAGCATATTTTCAATGATC |
|  | CA775_R1 | ATGCACCCGGGAAGGTCTTGAG |
|  | CA775_R2 | GAATCCCAGCTTTCAATGCACTTGG |
| 40 | CA717_R | CTCCTCCTCAATCTCATTTGTGG |
|  | CA717_R1 | GTGCCTTCAAGCATGCTGGAAGATG |
|  | CA717_R2 | GTGGTTCGGTCATCCCACCTTTGC |
|  | CA782_F1 | CCAATATTGGTGTATTATGAACAAGAG |
|  | CA782_F2 | CAGGCGTGCACGACTGATCCTC |
| 45 | CA783_F1 | GCAGCAGGAGGATGTAGAAC |
|  | CA783_F2 | CCAAATATTCTTCTTTTAGAATTGGCTTTGC |
|  | CA783_F3 | GAATTGGCTTTGCAAAATTTTGTTCTCTTGC |
|  | CA775_RB | CCTCACAAACACATCTGGTGATAC |
|  | CA775_R1B | CAGGGCAACCGTTTCAAGATC |
| 50 | CA775_R2B | CACTGACATCAGCAGTCTCAATCTGTGC |
|  | CA733_R | GAAGGAGAGGTACTGCACTTTC |
|  | CA733_R1 | CCCATCTGCCAATTGCTTC |

TABLE 2-continued

Primers used for 3'RACE and 5'RACE

| SEQ ID NO | Primer name | Sequence (5' to 3') |
|---|---|---|
|  | CA733_R2 | CATGCACTCTTCAGTGGTACCATATGTGTC |
|  | CA775_R1_marath | GGTGATCCAAGCATAGACGCTCCAATG |
| 55 | CA775_R2_marath | CGATGAGCTGCAGCCTACTAGCAGTAGTTG |
|  | dTadaptor | AATTCGGTACCCGGGATCCTTTTTTTTTTTTTTTT |
| 57 | adaptorP | AATCGGTACCCGGGATCC |

Based on the three half-full-length sequences obtained after the 3'RACE, we designed specific reverse primers for use in 5'RACE. The 5'RACE System from Invitrogen was used. For this procedure, three primers were used for each cDNA (one to prime the reverse transcription, and two nested primers for the first and second PCR). The reverse transcription part of the protocol was adapted for transcripts with high GC content, as described by the manufacturer. The PCR was performed using the Platinum® Taq DNA polymerase (Invitrogen). For the first PCR, the template was 5 μL of dC-tailed cDNA, and a cDNA specific primer (Table 2) and the Abridged Anchor Primer (Invitrogen) were used. The cycling conditions were: 2 min at 94° C.; 35 cycles of 0.5 min at 94° C., 0.5 min at 55° C. and 2 min at 72° C.; and 10 min at 72° C. For the second PCR, the template was 5 μL of 100 fold diluted first PCR product, and a nested cDNA-specific primer (table 2) and the Universal Amplification Primer (Invitrogen). The cycling conditions for the second PCR were: 2 min at 94° C.; 12 cycles of 0.5 min at 94° C., 0.5 min at 68° C. for the first cycle and minus 1° C. for each subsequent cycle, and 2 min at 72° C.; 25 cycles of 0.5 min at 94° C., 0.5 min at 60° C. and 2 min at 72° C.; and 10 min at 72° C. The amplification products were evaluated, sub-cloned, and their sequence analyzed as described above.

The amplification of the 5' end succeeded for CA717 and CA733, and for these two clones the full-length nucleotide sequence could be reconstituted (Vet 717: SEQ ID NO: 1; Vet 733: SEQ ID NO: 2).

For CA775, a first 5'RACE using the same approach allowed amplification of an 820 bp fragment. The analysis of the sequence showed a 60 bp overlap with the CA775 3'RACE product but revealed that the 5'RACE was not complete and that a portion of the 5' end was still missing. A new set of primers was designed based on the 5'RACE sequence obtained (further close to the 5'-end) and the 5'RACE was repeated in the same condition. These permitted to obtain an additional 100 bp but the translation initiation codon was still missing.

A third set of primers was designed for use with the cDNA obtained with the Marathon cDNA synthesis Kit (Clontech). The amplification was performed on an Eppendorf Mastercycler Gradiant thermal cycler with the Advantage® 2 Polymerase Mix, as described by the manufacturer. This third 5'RACE provided a additional 100 bp sequence that finally contained the start codon and thus provided the full length nucleotide sequence (Vet 775, SEQ ID NO: 3).

Comparison of the aminoacid sequences deduced from the full-length sesquiterpene synthase-encoding cDNAs (named Vet717, Vet733 and Vet775, corresponding to SEQ ID NO: 4, 5 and 6, respectively) showed a relative low homology (FIG. 3) (identity ranging from 31 to 40%). The closest mach found in the public sequences databanks are putative sesquiterpenes sesquiterpene synthases sequences from Oryza sativa (Rice) and Zea mays (corn). For Vet717 and Vet775, the closest sequences are respectively 47% and 50% identical. Vet733 has relative high sequences homology (76.8% identity) with sequences of sesquiterpene synthases from Zea mays encoded by the nucleotide sequences with accession number AY518310 to AY518314 (Köllner et al (2004) The Plant cell 16(5), 1115-1131). The sequence at the N-term end of Vet755 differs from the two others and from other know sesquiterpene synthases: the N-terminal end is extended by 50 aminoacids and contains an unusual motif PAAAASSQQQQ (SEQ ID NO: 7). Such N-terminal additional sequence is unusual and does not resemble any known peptide signal sequence.

Example 4

Heterologous Expression in Bacteria of the Sesquiterpene Synthases from Vetiver

The Vet717 full-length cDNA was amplified from the Marathon cDNA library using the primers CA717_Nde and CA717_Kpn (Table 3) designed from the sequence information obtained by RACE. PCR was performed using the Pfu polymerase (Promega), in a final volume of 50 μl containing 5 μl of Pfu DNA polymerase 10× buffer, 200 μM each dNTP, 0.4 μM each forward and reverse primer, 2.9 units Pfu DNA polymerase and 5 μl of 100-fold diluted cDNA (prepared as described above using the Marathon™ cDNA Amplification Kit (Clontech)). The thermal cycling conditions were as follows: 2 min at 95° C.; 30 cycles of 30 sec at 95° C., 30 sec at 55° C. and 4 min at 72° C.; and 10 min at 72° C. The PCR product, consisting of the full-length Vet717 cDNA containing a NdeI site including the translation initiation codon and the KpnI site immediately after the stop codon, was purified on an agarose gel and eluted using the QIAquick® Gel Extraction Kit (Qiagen). The PCR product was digested with NdeI and KpnI and ligated into the pETDuet-1 plasmid (Novagen) digested with the same enzymes. Sequencing of the insert showed no sequence difference with the RACE products.

TABLE 3

Primers used for construction of the expression plasmids

| SEQ ID NO | Primer name | Sequence (5' to 3') |
|---|---|---|
| 58 | CA717_Nde | TACTGACATATGGCCAGCAGCAGTCCTGTCC |
| 59 | CA717_Kpn | TTGGTACCTCAACAAGCTCGCACAGAGTTAACGTACATG |
| 60 | 733_Nco | CTAGCCATGGCGCTTCCTGTAGCACATCGTTATTCC |
| | 733_Eco | CGGAATTCAATTGGGTACTGGCTTCACGAATAGTAGTTC |
| | 775_fus1-f | CACCCCAAGCCCATGGGGAGATATCTTCCTCGGCAACTC |
| | 775_fus1-r | GGAAGATATCTCCCCATGGGCTTGGGGTGAATGTCTG |
| | 775_fus2-f | GCTCGTTCTTCCATTGACAAGAACTGTGATGGAGTGCATG |
| 65 | 775_fus2-r | CACAGTTCTTGTCAATGGAAGAACGAGCGGATAAACTCAGG |
| | 775_fus_Nco | CTAGCCATGGCCAGCAGCAGTCCTGCTCCTCTG |
| | 775_fus_Eco | CGGAATTCAAATGGGGATCTTAAATGGTTCGGCC |
| | 775_mut_F2 | GACAATGACTACTGCAATGGTGACCCTTTTAG |
| | 775_mut_R2 | CTAAAAGGGTCACCATTGCAGTAGTCATTGTC |
| 70 | 775_mut1F | CACCCCAAGCCCTTGGGGAGATATC |
| | 775_mut1R | GATATCTCCCCAAGGGCTTGGGGTG |
| 72 | Vet775_Nco | CTAGCCATGGCGAACTGCAGCCTTACTATTTCTGCTACT |

The plasmid was then transferred into *E. coli* BL21 (DE3) cells (Novagen). Single colonies of transformed cells were used to inoculate 5 ml LB medium. After 5 to 6 hours incubation at 37° C., the cultures were cooled to a 20° C. and expression of the protein was induced with 0.5 mM IPTG. After over-night incubation the cells were collected by centrifugation, resuspended in 0.5 ml Extraction Buffer (50 mM MOPSO pH 7, 5 mM DTT, 10% glycerol) and sonicated 3 times 20 s. The cell debris were sedimented by centrifugation 30 min at 18,000 g and the supernatant containing the soluble proteins was recovered. Analysis by SDS-PAGE analysis revealed the production of a recombinant protein with the expected molecular weight.

In the same way, the Vet733 cDNA was amplified from the Marathon cDNA library using the primers 733_Nco and 733_Eco (Table 3) and ligated as a NdeI-EcoRI fragment into the pETDuet-1 expression plasmid. The constructs were verified by sequencing. The heterologous expression in BL21 (DE3) using these plasmids provided a recombinant protein clearly visible by SDS-PAGE.

For ligation of Vet775 into the pETDuet-1 expression plasmid, since the cDNA already contained two NdeI and one NcoI restriction sites (respectively at position 603, 1483 and 1020), the amplification was performed in two stages, using the overlap extension PCR strategy (Horton, R. M., Hunt, H. D., Do, S. N., Pullen, J. K. and Pease, L. R. (1989) Engineering hybrid genes without the use of restriction enzymes: gene splicing by overlap extension. Gene 77, 61-68), in order to introduce the NcoI and EcorI sites at the extremities and to remove the internal NcoI restriction site. Two separate PCR reactions were first performed: one with primers Vet775_Nco (introducing a NcoI site immediately before the start codon) and 775_mut_F2; the second with the primers 775_mut_R2 and 775_fus_Eco (introducing a EcoRI site immediately after the stop codon). The 775_mut_F2 and 775_mut_R2 primers are forward and reverse mutagenic primers with 32 nucleotides overlapping region and allowing the suppression of the NcoI recognition site at position 1020 in the cDNA without modifying the protein sequence (change the codon for Ala340 from GCC to GCA) (Table 3). The products from these two PCR were purified, combined and used as template in a last PCR were the full-length mutated Vet775 cDNA is amplified with the primers Vet775_Nco and 775_fus_Eco. The PCR product was then ligated between the NcoI and EcoRI restriction sites of the pETDuet-1 plasmid.

In addition, to evaluate the effect of the unusual N-terminal sequence of Vet775 on the expression in *E. coli* and on the enzymatic activity, we made two constructs consisting of removing portions of the N-terminal end of Vet775 and replacing them with the equivalent portion derived from Vet717. Two modified cDNA were thus made, Vet775_fus1 and Vet775_fus2. In the first construct, the 68 first codons were removed and replaced with the 24 N-terminal codons of Vet717. In the second construct, the 91 first codons were removed and replaced with the 42 N-terminal codons of Vet717. These construct were made by overlap extension PCR. For Vet775_fus1, a first PCR was performed using the primers 775_fus_Nco and 775_fus1-r and as template the Vet717 cDNA in pETDuet-1. A second PCR was performed with the primers 775_fus1-f and 775_fus_Eco and as template the Marathon cDNA library. The primers 775_fus1-f and 775_fus1-r contain an overlapping region of 29 nucleotides (Table 3). The PCR products from the two amplifications were purified and used as template in another PCR using as the primers 775_fus_Nco and 775_fus_Eco. The PCR product, consisting of the open reading frame of Vet775 with the 204 5'-end bp replaced by the 72 5'-end bp of Vet717 and flanked by the NcoI and EcorI restriction sites, was ligated in the pCR®2.1-TOPO vector using the TOPO TA cloning Kit (Invitrogen). The inserts from three separated clones were fully sequenced to ensure that there was no sequence variation. The plasmid was then used as template for site directed mutagenesis by overlap extension PCR to remove the two NcoI sites at position 72 and 888 in nucleotidic sequence. This last modification was performed as described above by generating three overlapping fragments using the mutagenic primers pairs 775_mut_F1 and 775_mut_R1 (change the codon for Pro24 from CCA to CCT) (Table 3) and 775_mut_F2 and 775_mut_R2 (described above). The PCR product was finally ligated between the NcoI and EcoRI restriction sites of the pETDuet-1 plasmid. The construction of the cDNA coding for the Vet775_fus2 was made in the same way using the primers 775_fus2-f and 775_fus2-r (Table 3) in the first PCR to produce a cDNA consisting of nucleotides 1-126 for Vet717 fused to the nucleotides 274 to 1521 fro Vet775.

All these PCR for the amplification of the full-length or modified Vet775 cDNA were performed with the Pfu DNA polymerase as described above.

Heterologous expression in *E. coli* BL21(DE3) followed by SDS-PAGE analysis showed the production of a recombinant protein for the Vet775_fus1 and Vet775_fus2 constructs, but no recombinant protein was seen for the full-length non-modified Vet775.

Example 5

Characterization of the Enzyme Activities of the Recombinant Sesquiterpene Synthases The recombinant proteins obtained were assayed for sesquiterpene synthase activity using FPP as substrate. The enzymatic assays were performed in Teflon sealed glass tubes using 50 to 100 µl of crude *E. coli* protein extract, obtained following the procedure given in Example 3 (following Table 3) in a final volume of 1 mL Extraction Buffer supplemented with 15 mM $MgCl_2$ and 100 to 250 µM purified FPP. The media were overlaid with 1 ml pentane and the tubes incubated 12 to 18 hours at 30° C.

The sesquiterpenes produced were extracted twice with pentane and analyzed by GC and GC/MS as described previously (WO 04/031376, Example 6).

Enzymes assays with protein extracts obtained from cultures of *E. coli* transformed with the expression plasmids containing the Vet775 Full-length cDNA or the two Vet775 fusion proteins, did not permit to detect any sesquiterpene synthase activity. The reasons for this apparent inactivity remain undetermined.

The Vet717 recombinant protein (SEQ ID NO: 4) produced a major sesquiterpene hydrocarbon and several minor products (FIG. 4). The mass spectrum of the major product matched the mass spectrum of cyclosativene ((6) in FIG. 1) and the rentention time of this major product lined up with the retention time of a cyclosativene standard, on an apolar (SPB-1, Supelco) as well as on a polar column (InnoWax, Hewlett-packard). Cyclosativene or derivatives thereof were never identified in vetiver oil. Among the many sesquiterpenes identified, the oxygenated cyclocopacamphane sesquiterpenes (FIG. 1) are the most structurally close to cyclosativene. Cyclocopacamphene (7) is the stereoisomer of cyclosativene (Kido F et al (1969) *Tetrahedron letters* 37, 3169-3172) and interestingly, oxygenated derivatives of cyclocopacamphene are present in relative large quantities, up to 4%, in vetiver oil (Homa et al (1970) *Tetrahedron letters* 3, 231-234; Weyerstahl et al (2000) *Flavour Frag. J.* 15, 61-83; Weyerstahl et al (2000) *Flavour Frag. J.* 15, 153-173; Weyerstahl et al (2000) *Flavour Frag. J.* 15, 395-412).

To distinguish the product of Vet717 from cyclosativene, I employed chiral GC chromatography using a Megadex-5 (MEGA s.n.c., Legnano, Italy) capillary column (12 m, 0.25 mm, 0.25 µm) with the initial oven temperature set at 60° C. for 2 min hold, followed by a ramp of 5° C./min to 150° C. and a second ramp of 20° C./min to 270° C. In these conditions, cyclosativene had a retention time of 5.60 min and was clearly separated from the Vet717 product that had a retention time of 5.75 min.

The Vet717 enzyme produces also several minor products which, based on the MS spectra, could have related structures such as cubebane or copaane skeletons.

The Vet733 recombinant protein (SEQ ID NO: 5) does not produce a major product but a mixture of at least 7 different sesquiterpene hydrocarbons (FIG. 5). The following compounds could be identified based on the MS spectra and comparison of the rentention index with published data: (1) cis-alpha-bergamotene, (2) trans-alpha-bergamotene, (3) epi-beta-santalene, (4) beta-bisabolene, and (5) trans-gama-bisabolene. They were further confirmed by comparison to in house standards containing beta-bisabolene, trans-gama-bisabolene, trans-alpha-bergamotene and cis-alpha-bergamotene. The structure of epi-beta-santalene was confirmed by comparison to a GC-MS analysis of opoponax extract.

The sesquiterpene hydrocarbons produced by Vet733, or derivatives of these sesquiterpenes, have never been isolated from vetiver oil. It could be possible that Vet733 is expressed at low level in the roots of vetiver and that the sesquiterpenes produced by this enzyme are present in the oil at a level to low to be detected. The alcohols derivatives of some of the products of Vet733, (Z)-(+)-epi-beta-santalol and (Z)-alpha-trans-bergamotol (FIG. 1), have been described as being important contributors to the scent of sandalwood oil (DE 3 205 320; Frater, G., Bajgrowicz, J. A, and Kraft, P. (1998) Fragrance Chemistry. Tetrahedron 456, 7633-7703.). The odour of vetiver is very complex and, among many others, the sandalwood-like note has been described for this oil. It could thus be possible that the sandalwood aspect could be related to the presence of trace amounts of oxygenated derivatives of the Vet733 products.

Drawing of the mechanistic scheme for the formation of the sesquiterpenes produced by Vet733 explains the relationship of the multiple products formed (FIG. 6). Each turnover cycle starts with the isomerization of FPP ((16) in FIG. 6) to nerolydol-pyrophosphate (NPP) (with rotation about the $C_2$-$C_3$ bond), followed by cyclization to the bisabolyl cation (17). The cyclization can then go on via several mechanisms. The beta-bisabolene and trans-gamma-bisbolene can be formed by deprotonation at $C_6$ or $C_{14}$ respectively. $C_2$-$C_7$ closure followed by deprotonation leads to cis- and trans-alpha-bergamotenes. $C_3$-$C_7$ closure, followed by Wagner-Meerwein rearrangement and deprotonation at $C_{15}$ leads to epi-beta-santalene. The Vet733 sesquiterpene synthase is the first cloned sesquiterpene synthase able to catalyse the cyclisation of FPP to the bisabolyl cation and subsequent cyclization to the bergamotane and santalane skeleton.

The invention claimed is:

1. An isolated nucleic acid comprising the nucleotide sequence as set out in SEQ ID NO: 2 and encoding a polypeptide capable of synthesising at least one bi-cyclic and/or tri-cyclic sesquiterpene comprising a bond between the $C_3$ and $C_7$ carbon atoms of farnesyl-pyrophosphate of formula (I)

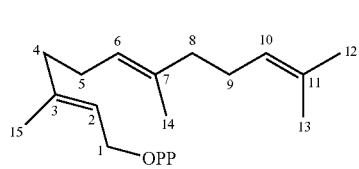

and optionally at least one bi-cyclic and/or tri-cyclic sesquiterpene comprising a bond between the $C_2$ and $C_7$ carbon atoms of farnesyl-pyrophosphate of formula (I).

2. An isolated nucleic acid according to claim 1, encoding a polypeptide comprising the amino acid sequence as set out in SEQ ID NO: 5.

3. An isolated nucleic acid according to claim 1, encoding a polypeptide capable of synthesising one or more sesquiterpenes including (+)-epi-β-santalene.

4. An isolated nucleic acid according to claim 1, encoding a polypeptide capable of synthesising one or more sesquiterpenes, including at least 5 wt. % of a compound having a bergamotene skeleton of formula (II),

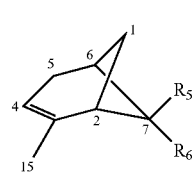

this percentage being relative to the total weight of the sesquiterpene products synthesised by the polypeptide.

5. An isolated nucleic acid according to claim 1, encoding a polypeptide capable of synthesising one or more bi- or tricyclic sesquiterpenes selected from the group of (+)-epi-β-santalene, trans-α-bergamotene, cis-α-bergamotene, β-bisabolene, and trans-γ-bisabolene.

6. An isolated polypeptide encoded by the isolated nucleic acid according to claim 1, comprising the amino acid sequence as set out in SEQ ID NO:5.

7. An isolated polypeptide according to claim 6, capable of synthesising one or more sesquiterpenes including (+)-epi-β-santalene.

8. An isolated polypeptide according to claim 6, capable of synthesising one or more sesquiterpenes, including at least 5 wt. % of a compound having a bergamotene skeleton of formula (II), this percentage being relative to the total weight of the sesquiterpene products synthesised by the polypeptide.

9. An isolated polypeptide according to claim 6, capable of synthesising one or more bi- or tricyclic sesquiterpenes selected from the group of (+)-epi-β-santalene, trans-α-bergamotene, cis-α-bergamotene, β-bisabolene, and trans-γ-bisabolene.

10. A vector comprising the nucleic acid according to claim 1.

11. A recombinant non-human host organism or cell transformed to harbour the nucleic acid according to claim 1, wherein said non-human host organism is a plant, a bacterium or a fungus and wherein said non-human host cell is a plant cell or a fungal cell.

12. A recombinant non-human host organism according to claim 11, wherein said bacterium is *E. Coli*.

13. A recombinant non-human host organism or cell according to claim 11, wherein said recombinant non-human organism or cell is transformed to express a polypeptide comprising the amino acid sequence as set out in SEQ ID NO: 5 in a higher quantity than in the same organism or cell not so transformed.

14. A method of making at least one terpenoid comprising
a) contacting the acyclic pyrophosphate terpene precursor with at least one polypeptide according to claim 6; and
b) optionally, isolating the at least one terpenoid produced in step a).

15. A method according to claim 14, wherein step a) comprises cultivating a non-human host organism or cell under conditions conducive to the production of at least one terpenoid, said non-human organism or cell being transformed to express a polypeptide encoded by the nucleic acid comprising the nucleotide sequence as set out in SEQ ID NO: 2 or transformed to express said polypeptide in a higher quantity than in the organism not so transformed, wherein said non-human host organism is a plant, a bacterium or a fungus and wherein said non-human host cell is a plant cell or a fungal cell.

16. A method according to claim 15, wherein step a) comprises transforming the non-human host organism or cell with a recombinant nucleic acid comprising the nucleotide sequence as set out in SEQ ID NO: 2 to express a polypeptide encoded by said nucleic acid or to express said polypeptide in a higher quantity than in the non-human host organism or cell not so transformed.

17. A method of making a terpene synthase comprising the step of cultivating a non-human host organism or cell according to claim 11 under conditions conducive to the production of said terpene synthase.

* * * * *